(12) United States Patent  (10) Patent No.: US 7,915,005 B2
Shaw et al.  (45) Date of Patent: Mar. 29, 2011

(54) METHODS FOR DETECTING SLEEPINESS

(75) Inventors: Paul Shaw, St. Louis, MO (US);
Laurent Seugnet, St. Louis, MO (US);
Stephen Duntley, St. Louis, MO (US);
Jaime Boero, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 850 days.

(21) Appl. No.: 11/558,074

(22) Filed: Nov. 9, 2006

(65) Prior Publication Data
US 2007/0105180 A1 May 10, 2007

Related U.S. Application Data

(60) Provisional application No. 60/735,143, filed on Nov. 9, 2005.

(51) Int. Cl.
*C12Q 1/40* (2006.01)
(52) U.S. Cl. .......................... 435/22; 600/573
(58) Field of Classification Search .................... 435/22; 600/573
See application file for complete search history.

(56) References Cited

U.S. PATENT DOCUMENTS

| | | | |
|---|---|---|---|
| 3,518,164 A | 6/1970 | Andelin et al. | |
| 4,283,498 A | 8/1981 | Schlesinger | |
| 4,580,577 A | 4/1986 | O'Brien et al. | |
| 4,589,548 A | 5/1986 | Fay | |
| 4,768,238 A | 9/1988 | Kleinberg et al. | |
| 5,286,262 A | 2/1994 | Herweck et al. | |
| 6,837,988 B2 | 1/2005 | Leong et al. | |
| 6,939,312 B2 | 9/2005 | Hodges et al. | |
| 2003/0054377 A1* | 3/2003 | Rosen et al. | 435/6 |
| 2003/0143113 A2 | 7/2003 | Yuzhakov et al. | |

OTHER PUBLICATIONS

Keller et al. "Circadian pancreatic enzyme pattern and relationship between secretory and motor activity in fasting humans" J. Applied Physiology. Apr. 19, 2002.*
Parkkila et al. "Circadian periodicity in salivary carbonic anhydrase VI concentration", 1995, Acta Physiologica Scandinavica pp. 205-211, vol. 154.*
Rodhleder et al. "Psychosocial stress-induced activation of salivary alpha-amylase" as submitted by applicant.*
Abraham, U., et al., "Independent circadian oscillations of period 1 in specific brain areas in vivo and in vitro", 2005, Journal of Neuroscience, pp. 8620-8626, vol. 25.
Aluoch, A.O. et al., "Development of an oral biosensor for salivary amylase using a monodispersed silver for signal amplification", 2005, Analytical Biochemistry, pp. 136-144, vol. 340.
Andretic, R. et al., "Dopaminergic modulation of arousal in *Drosophila*", 2005, Current Biology, pp. 1165-1175, vol. 15.
Baldi, P., et al., "A bayesian framework for the analysis of microarray expression data: regularized t-test and statistical inferences of gene changes", 2001, Bioinformatics, pp. 509-519, vol. 17.
Balling, A. et al., "Are the structural changes in adult *Drosophila* mushroom bodies memory traces? Studies on biochemical learning mutants", 1987, Journal of Neurogenetics, pp. 65-73, vol. 4.

(Continued)

*Primary Examiner* — Max Hindenburg
*Assistant Examiner* — Renee Danega
(74) *Attorney, Agent, or Firm* — Polsinelli Shughart PC

(57) ABSTRACT

The invention generally provides a biomarker for sleepiness, a method for detecting sleepiness, and a method of identifying nucleic acids associated with sleepiness.

15 Claims, 13 Drawing Sheets

OTHER PUBLICATIONS

Bosch, J.A., et al., "Innate secretory immunity in response to laboratory stressors that evoke distinct patterns of cardiac autonomic activity", 2003, Psychosomatic Medicine, pp. 245-258, vol. 65.

Granger, D.A. et al., "Integrating biological, behavioral and social levels of analysis in early child development: progress, problems and prospects", 2003, Child Development, pp. 1058-1063, vol. 74.

Harris, D.M. et al., "Stimulation of amylase release by orexin is mediated by orexin 2 receptor in AR42J cells", 2002, Pancreas, pp. 405-410, vol. 25.

Hendricks, J.C., et al., "Rest in Drosophila is a sleep-like state", 2000, Neuron, pp. 129-138, vol. 25.

Hendricks, J.C., et al., "Gender dimorphism in the role of cycle (BMAL1) in rest, rest regulation, and longevity in Drosophila melanogaster", 2003, Journal of Biological Rhythms, pp. 12-25, vol. 18.

Hendricks, J.C., et al., "Modafinil maintains waking in the fruit fly Drosophila melanogaster", 2003, Sleep, pp. 139-146, vol. 26.

Hickey, D.A., et al., "A Drosophila gene promoter is subject to glucose repression in yeast cells", 1994, Proceedings of the National Academy of Sciences, pp. 11109-11112, vol. 91.

Huber, R., et al., "Sleep homeostasis in Drosophila melanogaster", 2004, Sleep, pp. 628-639, vol. 27.

Kaufman, E., et al., "Analysis of saliva for periodontal diagnosis", 2000, Journal of Clinical Periodontology, pp. 453-465, vol. 27.

Keller, J., et al., "Circadian pancreatic enzyme pattern and relationship between secretory and motor activity in fasting humans", 2002, Journal of Applied Physiology, pp. 592-600, vol. 93.

Li, Y., et al., "Salivary transcriptome Diagnostics for oral cancer detection", 2004, Clinical Cancer Research, pp. 8442-8450, vol. 10.

Long, A.D., et al., "Improved statistical inference from DNA microarray data using analysis of variance and a Bayesian statistical framework", 2001, The Journal of Biological Chemistry, pp. 19937-19944, vol. 276.

McLaren, J.W., et al., "Pupillometry in clinically sleep patients", 2002, Sleep Medicine, pp. 347-352, vol. 3.

Mahay, S., et al., "Effects of ageing on morphology, amylase release, cytosolic Ca2+ signals and acyl lipids in isolated rat parotid gland tissue", 2004, Molecular and Cellular Biochemistry, pp. 199-208, vol. 266.

Merritt, S.L., et al., "Pupil staging and eeg measurement of sleepiness", 2004, International Journal Psychophysiology, pp. 97-112, vol. 52.

Nater, U.M., et al., "Human salivary alpha-amylase reactivity in a psychosocial stress paradigm", 2005, International Journal of Psychophysiology, pp. 333-342, vol. 55.

Nater, U.M., et al., "Stress-induced changes in human salivary alpha-amylase activity-associations with adrenergic activity", 2005, Psychoneuroendocrinology, pp. 1-10.

Park, N.J. et al., "Characterization of RNA in saliva", 2006, Clinical Chemistry, pp. 988-994, vol. 52.

Parkkila, S., et al., "Circadian periodicity in salivary carbonic anhydrase VI concentration", 1995, Acta Physiologica Scandinavica, pp. 205-211, vol. 154.

Rohleder, N., et al., "Psychosocial stress-induced activation of salivary alpha-amylase", 2004, Annals of the New York Academy of Sciences, pp. 258-263, vol. 1032.

Sampson, E.J., et al., "Characterization and intermethod relationships of materials containing purified human pancreatic and salivary amylase", 1981, Clinical Chemistry, pp. 714-720, vol. 27.

Seugnet, L., et al., "Identification of a biomarker for sleep drive in flies and humans", 2006, Proceedings of the National Academy of Sciences, pp. 19913-19918, vol. 103.

Shaw, P.J., et al., "Correlates of sleep and waking in Drosophila melanogaster", 2000, Science, pp. 1834-1837, vol. 287.

Shaw, P.J., et al., "Stress response genes protect against lethal effects of sleep deprivation in Drosphila", 2002, Nature, pp. 287-291, vol. 417.

Skosnik, P.D., et al., "Modulation of attentional inhibition by norepinephrine and cortisol after psychological stress", 2000, International Journal of Psychophysiology, pp. 59-68, vol. 36.

Streckfus, C.F., et al., "Saliva as a diagnostic fluid", 2002, Oral Diseases, pp. 69-76, vol. 8.

Takai, N., et al., "Effect of psychological stress on the salivary cortisol and amylase levels in healthy young adults", 2004, Archives of Oral Biology, pp. 963-968, vol. 49.

Toledo et al., "Identification of sleep regulatory genes in a sensitized Drosophila mutant using cDNA microarrays" Annual Meeting of the Professional Sleep Societies, Philadelphia.

Van Dongen, H.P., et al., "Individual differences in adult human sleep and wakefulness: Leitmotif for a research agenda", 2005, Sleep, pp. 479-496, vol. 28.

Van Stegeren, A., et al., "Salivary alpha amylase as marker for adrenergic activity during stress: effect of betablockade", 2005, Psychoneuroendocrinology, pp. 1-5.

Whitten, R.O., et al., "Three methods compared for isoamylase separation in tissue homogenates", 1988, Clinical Chemistry, pp. 1556-1560, vol. 34.

Yamaguchi, M., et al., "Performance evaluation of salivary amylase activity monitor", 2004, Biosensors and Bioelectronics, pp. 491-497, vol. 20.

* cited by examiner

METHODS FOR DETECTING SLEEPINESS

CROSS REFERENCE TO RELATED APPLICATIONS

This application claims priority from U.S. Provisional Application Ser. No. 60/735,143 filed on Nov. 9, 2005, hereby incorporated by reference in its entirety.

FIELD OF THE INVENTION

The present invention generally relates to biomarkers for sleepiness. More specifically, the present invention relates to a method of detecting sleepiness, a biomarker for sleepiness, and a method of identifying nucleic acids associated with sleepiness.

BACKGROUND OF THE INVENTION

Forced and self-inflicted sleep loss have reached epidemic proportions in western industrialized populations, costing billions of dollars in lost productivity and creating hazardous conditions on our roadways, in our skies and in our hospitals. Unfortunately, there is no simple quantifiable marker that can detect excessive sleepiness in a subject before the sleepiness results in a serious accident. To be effective, a marker for sleepiness should be responsive to increasing levels of sleep debt and should only be activated by periods of waking that are followed by compensatory increases in sleep time (sleep homeostasis).

A biomarker that can distinguish between subjects who are awake and excessively sleepy and subjects who are awake and well rested has not been identified. Thus, there is a need for a readily accessible biomarker that is responsive to sleepiness in humans.

BRIEF SUMMARY OF THE INVENTION

Among the several aspects of the invention is provided a method for detecting sleepiness in a subject. The method comprises measuring the level of amylase in the subject, wherein an elevated level of amylase in comparison to a baseline level of amylase indicates sleepiness.

Another aspect of the invention provides a biomarker for sleepiness in a subject. The biomarker comprises the level of amylase in the subject.

A further aspect of the invention provides a method for identifying a nucleic acid sequence associated with sleepiness. The method comprises in part comparing a first nucleic acid expression profile and a second nucleic acid expression profile of a nucleic acid expression profile set. The first nucleic acid expression profile and the second nucleic acid expression profile are selected from the group consisting of the following sets: the set comprising a first nucleic acid expression profile from a partially sleep resistant organism taken from at least one time point during resistance to sleep deprivation and a second nucleic acid expression profile of the partially sleep resistant organism taken from at least one time point during normal response to sleep deprivation, the set comprising a first nucleic acid expression profile from an organism exposed to a pharmacological agent that increases waking and induces corresponding sleep compensation and a second nucleic acid expression profile from an organism exposed to a pharmacological agent that increases waking and does not induce corresponding sleep compensation, and the set comprising a first nucleic acid expression profile from a sleep deprived organism with a corresponding activation of the homeostatic sleep response and a second nucleic acid expression profile from a sleep deprived organism without a corresponding activation of the homeostatic sleep response. The method further comprises identifying a difference in the expression of a nucleic acid between the first nucleic acid expression profile and the second nucleic acid expression profile of a nucleic acid expression profile set, wherein a difference indicates that the nucleic acid is associated with sleepiness.

DETAILED DESCRIPTION OF THE PREFERRED EMBODIMENTS

Figure 1:
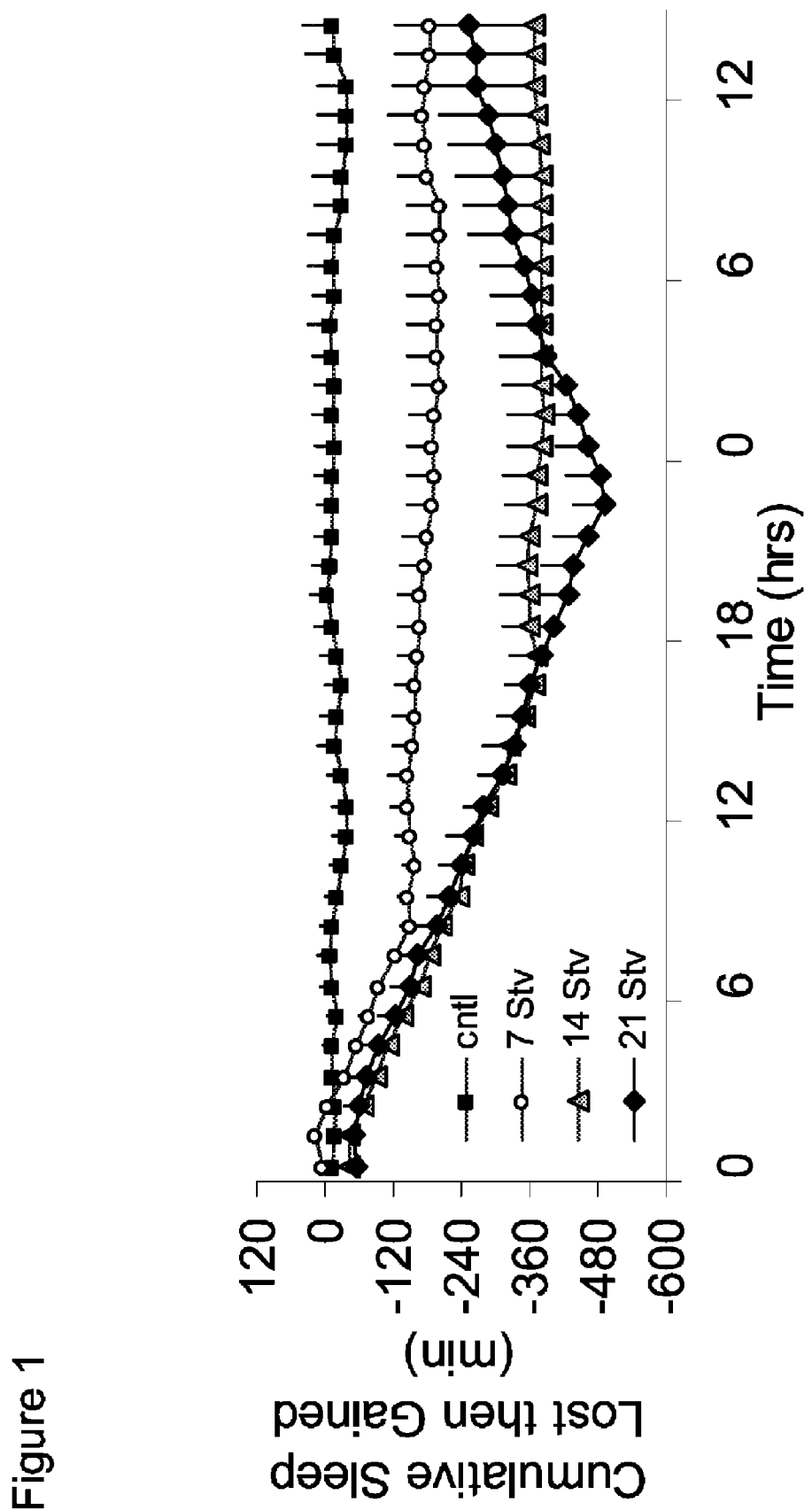
FIG. 1 illustrates that starvation increases waking. Cumulative sleep lost then gained during 7, 14 and 21 hours of starvation in $cyc^{01}$ mutants. A negative slope indicates sleep lost, a positive slope indicates sleep gained; when the slope is zero recovery is complete. Note that no fatalities were observed in any experiment and the flies could withstand over 14 h of wakefulness without showing signs of a homeostatic response.

Using the genetics of Drosophila melanogaster, a biomarker that is highly correlated with sleepiness, the level of amylase, has been identified. The level of amylase, as detailed in the examples, has been shown to be responsive to sleep deprivation in a variety of subjects, including humans, making this readily accessible enzyme a suitable biomarker for identifying and/or predicting dangerous levels of sleepiness. As such, the present invention provides biomarkers and methods that can be used to distinguish between subjects who are awake and excessively sleepy and subjects who are awake and well rested. The method of the invention can thus be used to identify and predict dangerous levels of sleepiness, especially in vulnerable populations, such as pilots, doctors, and commercial truck drivers.

I. Use of Amylase as a Biomarker to Detect Sleepiness

One aspect of the invention provides methods that generally utilize the level of amylase as a biomarker to detect sleepiness in a subject. Specifically, as detailed in the examples, it has been discovered that the level of amylase is highly correlated with sleepiness: the level of amylase is typically elevated in a subject who is sleepy and is typically not elevated when the subject is not sleepy. The method typically comprises measuring the level of amylase in a subject such that an elevated level of amylase compared to a baseline level of amylase indicates sleepiness.

In one embodiment, a baseline level of amylase may be the level of amylase in a well-rested subject, such that an elevated level of amylase in the same subject, compared to the baseline level of amylase, indicates sleepiness. In an alternative embodiment, a baseline level of amylase may refer to the average level of amylase in a particular population, measured when the population is well-rested, such that an elevated level of amylase of an individual of the population, compared to the baseline level of amylase for the population when well-rested, indicates sleepiness. Methods of measuring whether a subject is well-rested are known in the art, and include the Stanford sleepiness scale.

Generally speaking, the level of amylase is measured in a biosample taken from the subject. Several biosamples are suitable for use in the present invention to the extent the biosample has quantifiable levels of amylase that vary depending upon the sleep status of the subject. A variety of amylase isoforms may be measured according to the practice of the invention. For example, there are several types of amylase, including two major isoenzymes, pancreatic type amylase (P-type amylase) and salivary type amylase (S-type amylase), both of which are α-amylases. Generally speaking, P-type amylase is organ-specific, being almost exclusively attributed to the pancreas, whereas S-type amylase is not organ-specific and may be found in tears, sweat, human milk, amniotic fluid, the lungs, testes, and the epithelium of the fallopian tube. Examples of suitable biosamples, as such, may include a blood sample, an interstitial fluid sample, a gastrointestinal sample, a tear sample, a breath sample, a saliva sample, a fecal sample, a urine sample, a pancreatic juice sample, a semen sample, and a vaginal fluid sample. In certain embodiments, the biosample may be selected from the group consisting of a saliva sample, a pancreatic sample, and a blood sample. In a further embodiment, the biosample comprises a saliva sample.

As will be appreciated by a skilled artisan, the method of collecting a biosample from a subject can and will vary depending upon on the nature of the biosample. Any of a variety of methods generally known in the art may be utilized to collect a biosample from a subject. Generally speaking, the method preferably maintains the integrity of the amylase such that it can accurately be quantified in the biosample.

In one embodiment, the biosample is blood. Various methods of collecting blood are known in the art. Some of these methods are directed toward hospital applications (see U.S. Pat. No. 5,286,262), while others are directed more toward personal use at home or elsewhere, i.e., handheld glucose monitoring systems (see U.S. Patent Application 20030143113). Generally, a method of collecting blood comprises accessing the blood using a skin-piercing element and collecting the blood therein into some type of a collection device. Accessing the blood may also involve the use of a fluid pathway, a capillary channel (e.g., a capillary tube), a fluid transfer medium (e.g., a hydrophilic porous material), or some kind of mechanical or vacuum means in conjunction with the skin-piercing element. The steps of accessing the blood sample, collecting the biosample, and measuring the level of amylase in the biosample may be performed as separate steps with separate devices or these steps may be combined and performed using one device.

In an alternative embodiment, the biosample is interstitial fluid. Methods of collecting interstitial fluid are disclosed in U.S. Pat. No. 6,837,988 and U.S. Pat. No. 6,939,312, which are hereby incorporated by reference in their entirety. Generally, a method of collecting interstitial fluid is similar to the method disclosed above with regard to blood. Typically, when accessing interstitial fluid, the skin-piercing element has a reduced penetration depth, as compared to blood; typical skin-piercing elements for accessing interstitial fluid include micro-piercing elements. In certain aspects of the invention, the skin-piercing element is selected from the group consisting of a microneedle, microlancet, or another micro-piercing element. In some particular aspects, a micro-piercing element is present in conjunction with one or more elements selected from the group consisting of a fluid pathway, a fluid medium, a vacuum means, and a mechanical means.

In yet another alternative embodiment, the biosample is saliva. Several suitable methods of collecting saliva are known in the art, ranging from expectoration into a container to the use of an absorbent collection device, i.e., an absorbent swab. Various methods and apparatuses for collecting saliva have also been disclosed and by way of non-limiting example include methods disclosed in U.S. Pat. No. 4,589,548, U.S. Pat. No. 4,580,577, U.S. Pat. No. 4,283,498, U.S. Pat. No. 3,518,164, and U.S. Pat. No. 4,768,238, which are hereby by incorporated by reference in their entirety.

In a further embodiment, the biosample is pancreatic juice. Several methods of collecting a sample of pancreatic juice are known in the art. For example, a sample of pancreatic juice may be obtained by a conventional duodenal tube after exogenous secretin; the duodenal tube aspirates pancreatic juice from the duodenum. Alternatively, a sample of pancreatic juice may be obtained by endoscopic cannulation.

In an additional embodiment, the biosample is urine. A variety of methods of collecting a urine sample are also known in the art. Typically, for example, the subject urinates into a sterilized container, such as a cup.

It is contemplated that a variety of biomolecular forms of amylase may be measured in the biosample to determine the sleep status of the subject. In one embodiment, the level of amylase refers to the level of amylase mRNA in a biosample. In another embodiment, the level of amylase refers to the level of amylase transcription. In yet another embodiment, the level of amylase refers to the level of amylase translation. In still yet another embodiment, the level of amylase refers to the level of amylase protein in a biosample. In an alternative embodiment, the level of amylase refers to the level of amylase enzymatic activity.

A variety of methods known in the art are suitable to measure the level of amylase mRNA in a biosample. In some embodiments, the amylase mRNA may be purified prior to measurement. For example, mRNA may be purified according to the Trizol® method, from Invitrogen™ or using various kits manufactured by Quiagen, such as the Oligotex Direct mRNA Micro Kit. The level of amylase mRNA may be measured by several methods known in the art, including, for example, northern blot, microarray, expression profiling, nuclease protection assay, RNase protection assay, S1 nuclease protection assay, RT-PCR, quantitative RT-PCR, in situ hybridization, or variants thereof. In an exemplary embodiment, the level of amylase mRNA is measured as detailed in the examples.

In another embodiment, amylase activity is measured. As used herein, "amylase activity" includes amylase enzymatic activity. Generally, activity may be measured by means known in the art, such as measurement of product formation, substrate degradation, or substrate concentration, at a selected point(s) or time(s) in a reaction. There are numerous known methods and kits for measuring activity generally and amylase activity specifically. Several suitable methods utilizing a number of different reagents for measuring amylase activity have been reported; these methods can be grouped according to the nature of the substrate (i.e., chromogenic, such as dyed starch), reaction scheme (i.e., coupled enzyme), or product of the reaction (i.e., saccharogenic) and include the starch-iodine (amyloclastic) method as well as the nephelometric method. Various commercial test kits may be used to measure the level of amylase activity according to the present invention, including the Salimetrics α-Amylase Assay Kit (salivary amylase) and the Invitrogen EnzChek® UltraAmylase Assay. In an exemplary embodiment, the level of amylase activity is measured as detailed in the examples.

In a further embodiment, the level of amylase protein is measured. There are numerous known methods and kits for measuring the level of a protein in a sample. Non-limiting examples may include western blot, absorption measurement, calorimetric determination, Lowry assay, Bicinchoninic acid assay, or a Bradford assay. Commercial kits may include ProteoQwest™ Colorimetric Western Blotting Kits (Sigma-Aldrich, Co.), QuantiPro™ bicinchoninic acid (BCA) Protein Assay Kit (Sigma-Aldrich, Co.), FluoroProfile™ Protein Quantification Kit (Sig/*ma-Aldrich, Co.), the Coomassie Plus—The Better Bradford Assay (Pierce Biotechnology, Inc.), and the Modified Lowry Protein Assay Kit (Pierce Biotechnology, Inc.). Some methods may require purification of amylase protein prior to measuring the level of amylase enzymatic activity. Amylase protein may be purified according to any method known in the art, i.e., column chromatography or the method described in *Characterization and Intermethod Relationships of Materials Containing Purified Human Pancreatic and Salivary Amylase* (Sampson, et al., Clin. Chem. 27(5):714-20, 1981). In an exemplary embodiment, the level of amylase protein is measured as detailed in the examples.

In an alternative embodiment, the level of amylase transcription may be measured using techniques commonly known in the art. For instance, the level of amylase transcription may be measured by monitoring mRNA production through Northern blots or report gene assays. Additionally, the level of amylase translation may be measured using techniques commonly known in the art. For instance, the level of amylase translation may be measured using reporter protein assays.

II Types of Sleepiness

A variety of types of sleepiness or sleep related disorders may be detected according to the practice of the invention. The methods of the present invention, for example, can be used to distinguish between subjects who are awake and excessively sleepy and subjects who are awake and well rested. The term "sleepiness" is used broadly herein and encompasses sleep deprivation, coma, sleep fragmentation and disorders or conditions generally known in the art or otherwise described herein. Additionally, sleepiness may be used to refer to sleep drive. Numerous sleep disorders have been identified and may be diagnosed utilizing the methods of the invention. Sleep disorders can be grouped into four general categories: dyssomnias, parasomnias, sleep disorders associated with medical/psychiatric disorders, and proposed sleep disorders.

In one embodiment, the method is used to detect or treat a subject having a dyssomnia. Dyssomnias typically can be divided into three groups: intrinsic sleep disorders, extrinsic sleep disorders, and circadian rhythm sleep disorders. It is contemplated that the present invention may be utilized to diagnose and treat any of the aforementioned sleep disorders. Intrinsic sleep disorders include psychophysiological insomnia, sleep state misperception, idiopathic insomnia, narcolepsy, recurrent hypersomnia, idiopathic hypersomnia, post-traumatic hypersomnia, obstructive sleep apnea syndrome, central sleep apnea syndrome, central alveolar hypoventilation syndrome, periodic limb movement disorder, rhythmic movement disorder, and restless legs syndrome. Extrinsic sleep disorders include inadequate sleep hygiene, environmental sleep disorder, altitude insomnia, adjustment sleep disorder, insufficient sleep syndrome, limit-setting sleep disorder, sleep-onset association disorder, food allergy insomnia, nocturnal eating (drinking) syndrome, hypnotic-dependent sleep disorder, stimulant-dependent sleep disorder, alcohol-dependent sleep disorder, and toxin-induced sleep disorder. Circadian rhythm sleep disorders include time zone (jet lag) syndrome, shift work sleep disorder, irregular sleep-wake pattern, delayed sleep phase syndrome, advanced sleep phase syndrome, and non 24-hour sleep-wake disorder.

In an alternative embodiment, the method is used to detect or treat a subject having parasomnia. Parasomnias typically can be divided into three groups: arousal disorders, parasomnias usually associated with REM sleep, and other parasomnias. The present invention contemplates diagnosis and treatment of any of the aforementioned disorders. Arousal disorders include confusional arousals, sleepwalking, sleep talking, and sleep (or night) terrors. Parasomnias usually associated with REM sleep may include nightmares, sleep paralysis, impaired sleep-related penile erections, sleep-related painful erections, REM sleep-related sinus arrest, and REM sleep behavior disorder. Other parasomnias may include sleep bruxism, sleep enuresis, sleep-related abnormal swallowing syndrome, nocturnal paroxysmal dystonia, sudden unexplained nocturnal death syndrome, primary snoring, infant sleep apnea, congenital central hypoventilation syndrome, sudden infant death syndrome, and benign neonatal sleep myoclonus.

The method may also be used to diagnose and treat a subject having a sleep disorder associated with a medical or psychiatric condition. Sleep disorders associated with medical/psychiatric disorders can be grouped into three categories: those associated with mental disorders, those associated with neurological disorders, and those associated with other medical disorders. The present invention contemplates diagnosis and treatment of any of the aforementioned disorders. Sleep disorders associated with mental disorders may include psychoses, i.e., schizophrenia, mood disorders, i.e., bipolar disorder, depression, anxiety disorders, panic disorders, and alcoholism. Sleep disorders associated with neurological disorders may include cerebral degenerative disorders, dementia, parkinsonism, fatal familial insomnia, sleep-related epilepsy, electrical status epilepticus of sleep, and sleep-related headaches. Sleep disorders associated with other medical disorders may include sleeping sickness, nocturnal cardiac ischaemia, chronic obstructive pulmonary disease, sleep-related asthma, sleep-related gastroesophageal reflux, peptic ulcer disease, and fibrositis syndrome.

A variety of other sleep disorders may be diagnosed and treated according to the practice of the invention. These sleep disorders may include, for example, short sleeper, long sleeper, subwakefulness syndrome, fragmentary myoclonus, sleep hyperhidrosis, menstrual-associated sleep disorder, pregnancy-associated sleep disorder, terrifying hypnogogic hallucinations, sleep-related neurogenic tachypnea, sleep-related larnyngospasm, and sleep choking syndrome.

A variety of subjects may be diagnosed or treated according to the practice of the invention. The subject may be any human or animal subject who has sleepiness or a sleep disorder or sleep condition or who is at risk for developing any of the aforementioned indications. The subject may be a domestic livestock species, a laboratory animal species, a zoo animal or a companion animal. In one embodiment, the subject is a mammal. In an exemplary embodiment, the mammal is a human being. In certain aspects of the invention, the subject has been diagnosed with a sleeping disorder. Numerous sleeping disorders have been identified, as discussed in detail above. In some embodiments of the invention, the subject is at risk for sleepiness. Those at risk for sleepiness may include individuals with undiagnosed or untreated sleep disorders, i.e., untreated obstructive sleep apnea, business travelers, shift workers, individuals who work long hours, commercial drivers, i.e., long-haul drivers, young people—especially males under age 26, parents of young children, police officers, pilots, health professionals, i.e., physicians, military professionals, individuals being treated with certain sedating medications, i.e., anti-depressants, and individuals who have consumed alcohol or certain illegal drugs.

III. Kits for Detecting Sleepiness

Another aspect of the invention encompasses kits for detecting sleepiness in a subject. A variety of kits having different components are contemplated by the current invention. Generally speaking, the kit will include a means for detecting the level of amylase in a subject. In another embodiment, the kit will include means for collecting a biosample, means for measuring the level of amylase in the biosample, and instructions for use of the kit contents. In some aspects, the kit comprises a means for measuring the level of amylase mRNA. Preferably, the means for measuring the level of amylase mRNA comprises reagents necessary to detect the level of amylase mRNA. Such means of measuring the level of amylase mRNA as well as reagents necessary to detect the level of amylase mRNA are described in detail above. In certain embodiments, the kit comprises a means for measuring the level of amylase activity. Preferably, the means for measuring the level of amylase activity comprises reagents necessary to detect the level of amylase activity. Such means of measuring the level of amylase activity as well as reagents necessary to measure the level of amylase activity are described in detail above. In certain aspects, the kit comprises a means for measuring the level of amylase protein. Preferably, the means for measuring the level of amylase protein comprises reagents necessary to measure the level of amylase protein. Such means of measuring the level of amylase protein as well as reagents necessary to measure the level of amylase protein are described in detail above.

IV. Methods for Identifying Nucleic Acid Sequences Associated with Sleep

Another aspect of the present invention encompasses methods for identifying nucleic acid sequences associated with sleepiness. In part, these methods may be used to identify additional biomarkers for sleepiness. Generally speaking, the method for identifying a nucleic acid sequence associated with sleepiness comprises comparing a first nucleic acid expression profile and a second nucleic acid expression profile of a nucleic acid expression profile set and identifying a difference in the expression of a nucleic acid between the first nucleic acid expression profile and the second nucleic acid expression profile of a nucleic acid expression profile set, wherein a difference indicates that the nucleic acid is associated with sleepiness.

As used herein, "nucleic acid expression profile" refers to the level of expression of a plurality of nucleic acids isolated from an organism. Methods to evaluate nucleic acid expression are known in the art and include nucleic acid microarrays, PCR, and Northern blots. In one embodiment, nucleic acid microarrays are used to evaluate the nucleic acid expression. See http://www.ncbi.nlm.nih.gov/About/primer/microarrays.html for more details. Protocols to create and analyze microarrays are known in the art. In another embodiment, PCR is used to evaluate the nucleic acid expression. In a further embodiment, the PCR method is selected from the group comprising reverse transcriptase PCR, quantitative PCR, real-time PCR, and Touchdown PCR. PCR protocols are known in the art.

As used herein, "identifying a difference in expression of a nucleic acid" refers to identifying a nucleic acid sequence whose expression levels are statistically different between a first nucleic acid expression profile and a second nucleic acid expression profile. A difference in expression of a nucleic acid between a first nucleic acid expression profile and a second nucleic acid expression profile may indicate that the nucleic acid is associated with sleepiness, as detailed in the examples.

In each of the embodiments described herein, a nucleic acid expression profile may be derived from an organism. Generally speaking, the organism is a single species selected from the group comprising insects, amphibians, and mammals. In an additional embodiment, the organism is a single species selected from the group comprising insects. In an exemplary embodiment, the organism is a single species selected from the genus *Drosophila*. In another embodiment, the organism is from the species *Drosophila melanogaster*. In an alternative embodiment, the organism is a single species selected from the group comprising mammals. In a further alternative, the organism is a single species selected from the group comprising mice, rats, hamsters, and humans.

A. Nucleic Acid Expression Profile Set from a Partially Sleep Resistant Organism In one embodiment, the nucleic acid expression profile set comprises a first nucleic acid profile from a partially sleep resistant organism taken from at least one time point during resistance to sleep deprivation and a second nucleic acid expression profile of the partially sleep resistant organism taken from at least one time point during normal response to sleep deprivation.

The partial sleep resistant phenotype of the organism may be derived from a variant circadian clock gene. In one embodiment, the circadian clock gene may be derived from an organism selected from the group comprising insects, amphibians, and mammals. In an additional embodiment, the circadian clock gene may be derived from an organism selected from the group comprising insects. In another embodiment, the circadian clock gene may be derived from an organism selected from the genus *Drosophila*. In yet another embodiment, the circadian clock gene is derived from *Drosophila melanogaster*. In an alternative embodiment, the circadian clock gene may be derived from an organism selected from the group comprising mammals. In a further alternative, the circadian clock gene may be derived from an organism selected from the group comprising mice, rats, hamsters, and humans. In still a further embodiment, the circadian clock gene may be selected from the group comprising clock, cycle, period, cryptochrome, timeless, BMAL-1, Per-1, Per-2, Per-3, Cry1, and Cry2. In an exemplary embodiment, the circadian clock gene is timeless. In an additional embodiment, the variant circadian clock gene is $tim^{01}$.

The variant circadian clock gene can be 50, 60, 70, 80, 90, or 99% homologous to a circadian clock gene. In another embodiment, the variant circadian clock gene is 90, 95, 98, or 99% homologous to a circadian clock gene. In yet another embodiment, the variant circadian clock gene is 95, 96, 97, 98, or 99% homologous to a circadian clock gene. In determining whether a variant circadian clock gene is substantially homologous or shares a certain percentage of sequence identity with a circadian clock gene, sequence similarity may be determined by conventional algorithms, which typically allow introduction of a small number of gaps in order to achieve the best fit. In particular, "percent homology" of two nucleic acid sequences is determined using the algorithm of Karlin and Altschul (Proc. Natl. Acad. Sci. USA 87:2264-2268, 1993). Such an algorithm is incorporated into the NBLAST and XBLAST programs of Altschul et al. (J. Mol. Biol. 215:403-410, 1990). BLAST nucleotide searches may be performed with the NBLAST program to obtain nucleotide sequences homologous to a nucleic acid molecule of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are employed. See http://www.ncbi.nlm.nih.gov for more details.

The partial sleep resistant organism may be resistant to short-term sleep deprivation but not long-term sleep deprivation. In one embodiment, the nucleic acid expression profile of the organism is evaluated after a short-term sleep deprivation. In another embodiment, the nucleic acid expression profile of the organism is evaluated after about 0.5 to about 7.5 hours of sleep deprivation. In yet another embodiment, the nucleic acid expression profile is evaluated after about 1 to about 7 hours of sleep deprivation. In still yet another embodiment, the nucleic acid expression profile is evaluated after about 2 to about 6 hours of sleep deprivation. In an additional embodiment, the nucleic acid expression profile is evaluated after about 3 to about 6 hours of sleep deprivation. In an alternative embodiment, the nucleic acid expression profile of the organism is evaluated after a long-term sleep deprivation. In another embodiment, the nucleic acid expression profile of the organism is evaluated after about 7.5 to about 14 hours of sleep deprivation. In yet another embodiment, the nucleic acid expression profile of the organism is evaluated after about 8 to about 13 hours of sleep deprivation. In still yet another embodiment, the nucleic acid expression profile is evaluated after about 9 to about 12 hours of sleep deprivation.

B. Nucleic Acid Expression Profile Set from an Organism Exposed to a Pharmacological Agent In one embodiment the nucleic acid expression profile set comprises a first nucleic acid expression profile from an organism exposed to a pharmacological agent that increases waking and induces corresponding sleep compensation and a second nucleic acid expression profile from an organism exposed to a pharmacological agent that increases waking and does not induce corresponding sleep compensation.

Pharmacological agents that increase waking are known in the art. Some non-limiting examples include caffeine, methylphenidate, cocaine, amphetamine, methamphetamine, and modafinil. In one embodiment, a pharmacological agent that increases waking and induces corresponding sleep compensation is caffeine. In another embodiment, a pharmacological agent that increases waking and does not induce corresponding sleep compensation is methamphetamine.

C. Nucleic Acid Expression Profile Set from a Sleep Deprived Organism

In one embodiment, the nucleic acid expression profile set comprises a first nucleic acid expression profile from a sleep deprived organism with a corresponding activation of the homeostatic sleep response and a second nucleic acid expression profile from a sleep deprived organism without a corresponding activation of the homeostatic sleep response.

The organism deprived of sleep may be sleep sensitive. In one embodiment, the organism is sleep sensitive because of the expression of a variant circadian clock gene. In another embodiment, the circadian clock gene is derived from an organism selected from the group comprising insects, amphibians, and mammals. In an additional embodiment, the circadian clock gene is derived from an organism selected from the group comprising insects. In another embodiment, the circadian clock gene is derived from an organism selected from the genus *Drosophila*. In yet another embodiment, the circadian clock gene is derived from *Drosophila melanogaster*. In an alternative embodiment, the circadian clock gene is derived from an organism selected from the group comprising mammals. In a further alternative, the circadian clock gene is derived from an organism selected from the group comprising mice, rats, hamsters, and humans. In still a further embodiment, the circadian clock gene is selected from the group comprising clock, cycle, period, cryptochrome, timeless, BMAL-1, Per-1, Per-2, Per-3, Cry1, and Cry2. In an exemplary embodiment, the circadian clock gene is cycle.

In an additional embodiment, the variant circadian clock gene is $cyc^{01}$. The variant circadian clock gene can be 50, 60, 70, 80, 90, or 99% homologous to a circadian clock gene. In another embodiment, the variant circadian clock gene is 90, 95, 98, or 99% homologous to a circadian clock gene. In yet another embodiment, the variant circadian clock gene is 95, 96, 97, 98, or 99% homologous to a circadian clock gene. The methods used to determine percent homology are described above in section iv-a.

In an embodiment of the invention, sleep deprivation that does not activate a corresponding homeostatic sleep response is induced by starvation. In a further embodiment, sleep deprivation is induced by about 0, 1, 5, 10, 15, 20, 25, or 30 hours of starvation. In another embodiment, sleep deprivation is induced by about 2, 3, 4, 5, 6, 7, or 8 hours of starvation. In yet another embodiment, sleep deprivation is induced by about 9, 10, 11, 12, 13, 14, 15, 16, 17, or 18 hours of sleep deprivation. In still yet another embodiment, sleep deprivation is induced by about 19, 20, 21, 22, 23, 24, 25, 26, 27, 28, 29, or 30 hours of sleep deprivation.

In an alternative embodiment of the invention, sleep deprivation that does induce a corresponding activation of the homeostatic sleep response is induced by a method selected from the group comprising physical sleep disruption and mechanical sleep disruption. In another embodiment, the sleep disruption is induced by a physical sleep disruption. In yet another embodiment, the physical sleep disruption was induced by manually keeping the organism awake. In an alternative embodiment, the sleep disruption is induced by a mechanical sleep disruption. In a further embodiment, the mechanical sleep disruption is induced by a geotactic response. In an additional embodiment, the sleep disruption is induced by initiating a geotactic response about 6 to about 15 times per minute. In another embodiment, the sleep disruption in induced by initiating a geotactic response about 8 to about 12 times per minute. In yet another embodiment, the sleep disruption is induced by initiating a geotactic response about 10 times per minute. In an alternative embodiment, the mechanical sleep disruption is induced by moving a thin plastic strip that serves as the floor of the tube. The plastic strip is not wide enough for the fly to position itself completely on either the floor or the walls of the tube; as the floor slips beneath the fly, it is forced to walk. The distance the floor travels, the speed of the floor, the acceleration of the floor and the interval between the floor movements can all be varied to induce mechanical sleep disruption.

D. Combinations of Nucleic Acid Expression Profile Sets

The method for identifying a nucleic acid sequence associated with sleepiness may additionally comprise identifying a difference in expression of a nucleic acid between the first nucleic acid expression profile and the second nucleic acid expression profile of at least two nucleic acid expression profile sets. In some embodiments, the method may comprise identifying a difference in expression of a nucleic acid between the first nucleic acid expression profile and the second nucleic acid expression profile of at least three nucleic acid expression profile sets.

DEFINITIONS

As used herein, the term "behavioral method" refers to a method of identifying a nucleic acid sequence associated with sleepiness that utilizes different reactions to different behavioral interventions.

As used herein, a "circadian clock gene" refers to a gene involved in Circadian rhythm formation and regulation. A "variant circadian clock gene" is a homologue of a circadian clock gene, or a mutation of a circadian clock gene. In one embodiment, the mutation is selected from the group comprising point mutations, substitution mutations, frame-shift mutations, silent mutations, truncation mutations, and conservative mutations.

As used herein, "differentially expressed" means a statistical difference in nucleic acid expression levels between the two samples being analyzed. Statistical differences can be identified using the Cyber-T Bayesian statistical framework. For more information see http://molgen.biol.rug.nl/cybert/.

As used herein, the term "genetic method" refers to a method of identifying a nucleic acid sequence associated with sleepiness that utilizes partially sleep resistant organisms.

As used herein, "genetic profile" refers to the analysis of a number of different genes. A genetic profile could encompass the genes in an entire genome, or it could encompass a specific subset of genes.

As used herein, "homeostatic sleep response" refers to the natural cycle of accumulation of sleep debt during waking and the corresponding discharge of sleep debt through sleep.

As used herein, the term "pharmacological method" refers to a method of identifying a nucleic acid sequence associated with sleep that utilizes the different effects of pharmacological agents on sleep.

As used herein, "resistant to sleep" or "resistance to sleep deprivation" describes a phenotype wherein sleep deprivation is not accompanied by a corresponding sleep compensation.

As used herein, "sleep compensation" refers to the increased sleep that follows sleep deprivation.

As used herein, "sleep deprivation" means disrupting the natural sleep cycle. The sleep deprivation method can be selected from the group comprising physical, pharmacological, behavioral, or mechanical sleep disruptions. "Mechanical sleep disruption" refers to using a machine to help disrupt sleep. "Physical sleep deprivation" refers to using manual physical force to help disrupt sleep.

As used herein, the term "sleep sensitive" refers to an organism is subject to accelerated accumulation of the harmful effects of waking.

As used herein, "starvation" refers to withdrawing or withholding food for a specific amount of time. In one embodiment, fruit flies are starved by providing 1% agar as a nutritional source.

EXAMPLES

Example 1

Materials and Methods

Flies were cultured at 25° C., 50 to 60% humidity, 12 hr:12 hr Light:Dark cycle (LD), on yeast, dark corn syrup and agar food as described. $cyc^{01}$; ry and yw; $tim^{01}$ flies were obtained from J. C. Hall (Brandeis Univ.); Canton-S flies were obtained from the Bloomington Stock center; Amy/Luc flies were obtained from Donnel Hickey (University of Ottawa). Newly eclosed adult flies were collected from culture vials daily under $CO_2$ anesthesia.

Three day old female flies were placed in 65 mm glass tubes and sleep parameters were continuously evaluated throughout all experiments using the Trikinetics activity monitoring system as previously described (Shaw, P J et al., 2000. Science 287: 1834-1837; Shaw, P J et al., 2002. Nature 417: 287-291) (www.Trikinetics.com). Flies were sleep deprived (SD) using an automated sleep deprivation apparatus that has been found to produce waking without nonspecifically activating stress responses (Shaw, P J et al., 2000. Science 287: 1834-1837; Shaw, P J et al., 2002. Nature 417: 287-291). Three independent replicates of 32 flies were conducted for each time point. Following SD, two thirds of the flies from each group were frozen and RNA was extracted from whole heads. The remaining one third of the flies were monitored for an additional 24 h to assay the size of the homeostatic response. Using this protocol, both gene expression and behavior can be evaluated in siblings that have been exposed to identical environments and experimental manipulations.

Pharmacological studies were conducted on female Canton-s flies. Three-day old Cs female flies were individually placed into 65 mm glass tubes in the Trikinetics activity monitoring system and evaluated for two days under LD. After two days of baseline recordings, on day 3, two hours before the beginning of their primarily sleep period, flies were randomly assigned to receive caffeine (2.5 mg/mL), methamphetamine (0.5 mg/mL) or vehicle. All groups had similar amounts of baseline sleep. In all cases, the drug was dissolved in food along with an inert dye. It could be determined, therefore, if the fly had ingested the drug not only by its behavior, but also by observing the dye in its abdomen. The following morning, after 14 h of drug treatment, two thirds of the flies from each group were frozen and RNA was extracted from whole heads and the amount of dye in the abdomen was evaluated. The remaining one third of the flies were monitored for an additional 24 h to assay the size of the homeostatic response. We have found that the amount of dye in the abdomens of flies given caffeine and methamphetamine is not qualitatively different from vehicle fed controls. These results indicate that i) they are not starving themselves, ii) the drugs are not producing anorexic effects and iii) they are consuming the drug.

Amylase activity was evaluated following 28 h of sleep deprivation in Cs flies to match the duration of waking used in the human experiments. Female Cs flies were sleep deprived for 28 h beginning at lights out (8 pm). Whole body homogenates were extracted from 4 groups of 5 flies and compared to untreated circadian-matched controls; experiments were conducted in duplicate. Amylase activity was determined using the Infinity Amylase reagent (TR25421; Thermo Electron Corp, Louisville, Co., USA) according to the manufacturer's instructions. All samples were assayed in quadruplicate. To evaluate the effects of stress on amylase activity, Cs females were placed onto 20 μM paraquat dissolved in 1% agar 5% sucrose for 16 h and sacrificed at the same circadian time as the 28 h SD flies and their controls. We limited the duration on paraquat to 16 h because flies begin to die during longer exposures (Shaw, P J et. al., 2002. Nature 417: 287-291).

Prior to luminescence recordings, sleep was evaluated for 2 days in female Amy/Luc flies as described above with the exception that they were maintained on 0.5% sucrose supplemented with 1 mM beetle luciferin (Promega, Madison Wis.).

On day 3, flies were sleep deprived for 12 h (n=9) or served as untreated controls (n=9). Flies that were sleep deprived were removed from their 65 mm glass tubes and placed into Petri dishes with 200 µl of fresh 0.5% sucrose 1 mM beetle luciferin. Siblings that had not been sleep deprived were placed into Petri dishes with 2.5 mg/ml of caffeine added to the 0.5% sucrose 1 mM beetle luciferin. Bioluminescence was subsequently recorded in 1 min bins for 12 h under photomultiplier tubes (HC135-11MOD; Hamamatsu, Shizouka, Japan) as previously described (Abraham, U, et al., 2005. J Neurosci 25: 8620-8626). Amy/Luc flies that had never been exposed to luciferin were recorded for 12 h and served as a blank. Luminescence for SD and caffeine treated flies was subtracted from the blank and smoothed using a 3 h running average. Two independent replicates were conducted.

QPCR

Total RNA was isolated from fly heads using Trizol (Invitrogen, Carlsbad, Calif.) following the manufacturers protocol. Reverse transcription reactions were carried out in parallel on DNAse I digested total RNA. Reverse transcription products were stored at −80° C. until use. PCR reactions to measure levels of artificial transcript were done to confirm uniformity of reverse transcription within sample groups and between samples. Comparable reverse transcription reactions within a sample group were pooled. All reverses were performed in quadruplicate. A minimum of 2 QPCR replications were performed for each condition. Values were expressed as a percentage of untreated animals and were evaluated using a one-way ANOVA.

Human Subjects 9 healthy human adult volunteers (7 men and 2 women), were enrolled in the study after obtaining their consent. The study was approved by the Institutional Review Board at Washington University School of Medicine.

The subjects were randomly separated into two groups which where scheduled to alternate 2 weekends of either normal sleep or 28 hours of continuous waking. The sleep protocol was carried out at the Sleep Medicine Center, Department of Neurology, Washington University School of Medicine. On the normal sleep weekend, the volunteers were allowed to fall asleep at 10:00 pm. Normal sleep architecture and absence of significant respiratory abnormalities during sleep, periodic limb movement disorder, parasomnias, and nocturnal seizures were confirmed by standard polysomnography. The polysomnograms were evaluated and scored following standard criteria (Rechtschaffen, A. and Kales, A., editors (1968). A manual of standardized terminology, techniques and scoring system for sleep stages in human subjects. US Government Printing Office). The sleep deprivation group remained awake and was allowed free access to water during the night. However, meal times were restricted to 8 am, 12 noon, and 6 pm. No efforts were taken to limit caffeine consumption during the day, and logs were kept for each participant. The participants were constantly monitored by two experienced certified sleep technicians. Saliva was collected from plain (non-citric acid) cotton Salivettes (Sarstedt) after chewing for approximately 1 minute. The samples were rapidly frozen over dry ice and kept −80° C. until assayed. Total protein was evaluated in saliva using the Pyrogallol Red method (TP0400-1 KT, Sigma, Mo.). Amylase activity was evaluated by Salimetrics Analytical Laboratory Services using the Salivary α-Amylase Assay Kit (1-1902; Salimetrics, State College, Pa.). RNA was isolated from cell-free supernatant as described previously (Li et al., 2004. Clin Cancer Research 10:8442). RNA was treated with Rnase-free Dnase I (TURBO DNA-free, Ambion Inc., Austin, Tex., USA) according to the manufacturer's instructions. Isolated RNA was reverse transcribed using Superscript III (Invitrogen Life Technologies, Carlsbad, Calif., USA) according to the manufacturer's instructions. Q-PCR was performed with the use of an Applied Biosystems 7000 Real-Time PCR System (Applied Biosystems, Foster City, Calif., USA). Pre-designed TaqMan® Gene Expression Assays (Applied Biosystems, Foster City, Calif., USA) were used analyzing the mRNA levels of beta actin (ACTB) and Amylase. A 9 uL aliquot of the cDNA was used in each reaction, and all reactions were performed in duplicate.

Example 2

Behavioral Method of Identifying Nucleic Acid Sequences Associated with Sleep

Figure 2:
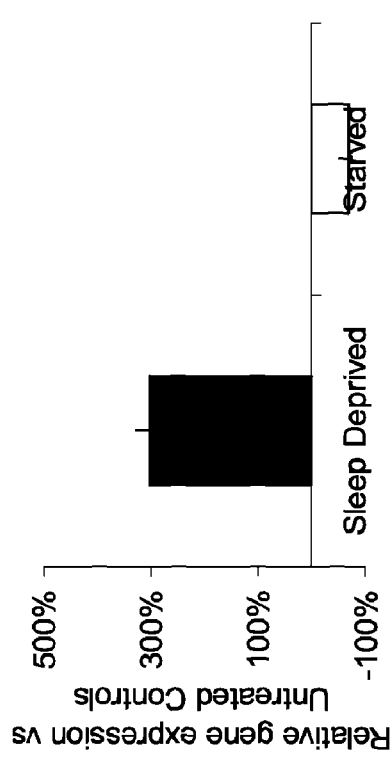
FIG. 2 illustrates that the cost of waking can be reduced by experimental intervention. Cumulative sleep lost then gained during 7 h of sleep deprivation (triangles) and 7 h of starvation (squares) in $cyc^{01}$ flies (FIG. 2A). A negative slope indicates sleep lost, a positive slope indicates sleep gained; when the slope is zero recovery is complete. Hashed bars indicate treatment. $cyc^{01}$ flies show an exaggerated homeostatic response to 7 h of sleep deprivation but do not compensate for sleep lost during starvation. Relative expression of CG18640 (an amylase) vs. untreated controls in $cyc^{01}$ flies immediately following 7 h of sleep deprivation and 7 h of starvation (FIG. 2B). $per^{01}$ flies show a homeostatic response to 7 h of sleep deprivation but do not compensate for lost sleep during starvation (FIG. 2C). Relative expression of CG18640 (an amylase) vs. untreated controls immediately following 7 h of sleep deprivation and 7 h of starvation (FIG. 2D). CG18640 encodes a protein that binds calcium ions and displays α-amylase activity.
Figure 2:
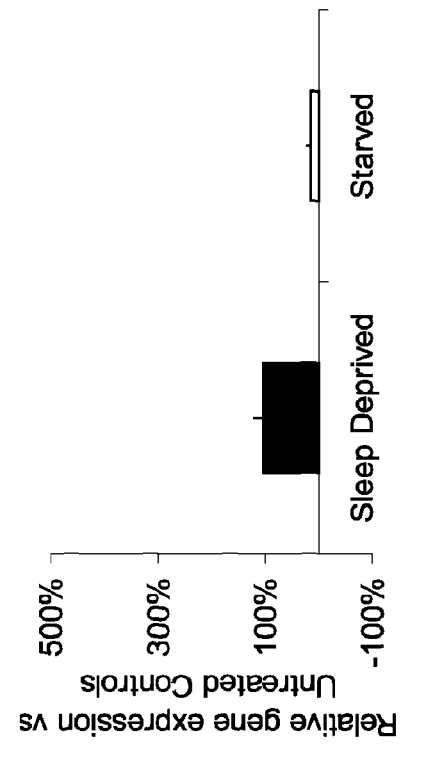
Figure 2:
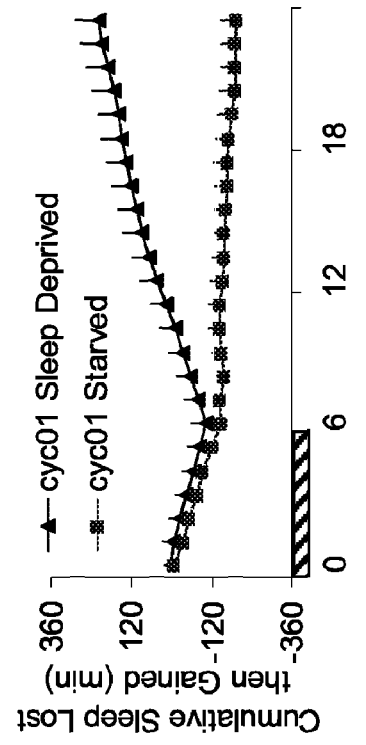
Figure 2:
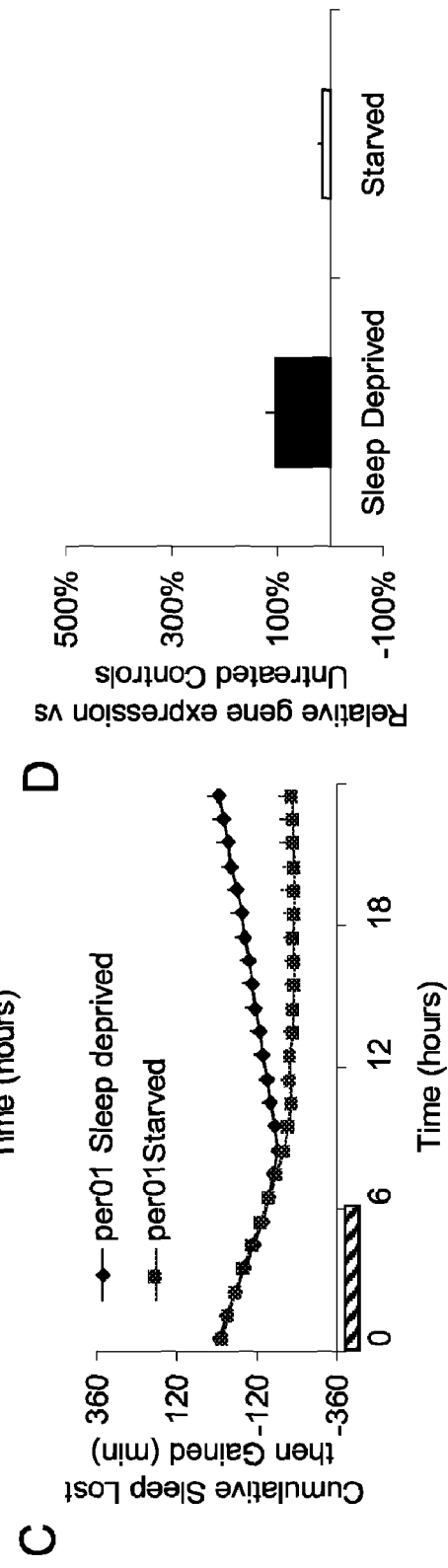

When starved, flies show an immediate and sustained increase in wake time (FIGS. 1, 2A, C). However, flies do not exhibit a homeostatic response when placed back onto food indicating that homeostatic mechanisms had not been activated (FIGS. 1, 2A and C). The response is not specific to one particular mutation or genetic background and has been observed in various mutant lines and wild-type flies. To further characterize genes associated with homeostasis, flies that have been awake and accrue sleep debt have been compared to their siblings that have been awake but that do not demonstrate a subsequent sleep rebound. In this way, genes can be identified that accelerate the cost of waking and are uniquely associated with activating homeostatic mechanisms.

Three-day-old female $cyc^{01}$ mutants were monitored under baseline conditions for 2 days. On the third day, they were either sleep deprived for 7 h according to standard procedures (Shaw, P J et. al., 2002. Nature 417: 287-291) or starved for 7 h by replacing their food with 1% agar. The fly's behavior was evaluated during the treatment at which time, two thirds of the flies and their untreated controls were frozen so that RNA could be extracted from whole heads. The remaining one third of the flies were placed into tubes containing fresh food and their behavior was monitored for an additional 24 h to assay the size of the homeostatic response (FIG. 2A). Twenty independent experiments were conducted over 4 months to ensure that the results would be reproducible. Initially eight microarray replicates were performed each, for sleep deprived, starved and control $cyc^{01}$ flies using partial cDNA microarrays processed at the UCSD Biogem Biomedical Microarray Facility (Toledo et al. 2004. Identification of Sleep Regulatory Genes in a Sensitized Drosophila Mutant Using cDNA Microarrays., pp. in Annual Meeting of the Professional Sleep Societies, Philadelphia). Subsequently, three additional replicates were conducted on Affymetrix arrays at the Siteman Cancer Center Bioinformatics Core at the Washington University Medical School in St. Louis.

Attention was focused on identifying differences between $cyc^{01}$ flies that were kept awake by sleep deprivation vs. those that were kept awake by starvation in order to determine gene that increase the cost of waking. Statistical differences were identified using the Cyber-T Bayesian statistical framework (http://molgen.biol.rug.nl/cybert/) (Baldi, P, and A D Long, 2001. Bioinformatics 17: 509-519; Long, A D, et al., 2001. J Biol Chem 276: 19937-19944). Results indicated that approximately 100 genes were differentially activated by enforced waking compared to waking induced by starvation. Each of these genes was then evaluated using real-time quantitative PCR (qPCR) to establish the validity of the microarray result (see material and methods). The expression level of amylase was confirmed using qPCR and is shown in FIG. 2B.

The data are expressed as percent change from untreated controls to emphasize the direction of the modification. Note that a similar profile was observed in per$^{01}$ mutants undergoing the same treatment (FIGS. 2C, D). A representative list of genes that we have confirmed using qPCR is shown in Table 1. Once again, the data are presented as percent change from baseline such that a value of 100% is equivalent to a 2-fold change.

TABLE 1

Confirmation of microarray data. qPCR results were performed in quadruplicate and are expressed as percent change from untreated controls.

| | Gene | SD | Starved |
|---|---|---|---|
| 1 | BG: DS00464 | 1148% | 241% |
| 2 | AttA | 827% | −22% |
| 3 | CG10814 | 799% | 205% |
| 4 | CG13868 | 703% | 253% |
| 5 | cher | 700% | 366% |
| 6 | CG11050 | 642% | 271% |
| 7 | CG5295 | 501% | 165% |
| 8 | BG: DS05899 | 458% | 1684% |
| 9 | CG3672 | 327% | 114% |
| 10 | CG18640 | 301% | −68% |
| 11 | CG6687 | 301% | 112% |
| 12 | CG16926 | 296% | 29% |
| 13 | aay | 287% | 38% |
| 14 | CG13624 | 283% | 229% |
| 15 | Gfat2 | 218% | 15% |
| 16 | CG10383 | 192% | 38% |
| 17 | mub | 187% | 58% |
| 18 | bun | 177% | 35% |
| 19 | CG3505 | 162% | 61% |
| 20 | CG1600 | 156% | 5% |
| 21 | CG10668 | 149% | 54% |
| 22 | Tsp42El | 147% | 51% |
| 23 | Men | 142% | −28% |
| 24 | CG9461 | 142% | −1% |
| 25 | CG3074 | 137% | 21% |
| 26 | CG6330 | 114% | −20% |
| 27 | serpin-27A | 109% | 37% |
| 28 | Sodh-1 | 108% | 287% |
| 29 | glob1 | 105% | 32% |
| 30 | l(2)35Bg | 101% | 20% |
| 31 | EP2237 | 94% | 6% |
| 32 | Taf150 | 92% | 56% |
| 33 | CG3493 | 75% | 81% |
| 34 | CG17509 | 74% | −1% |
| 35 | Lk6 | 65% | 51% |
| 36 | LIMK1 | 64% | 36% |
| 37 | CG9628 | 63% | 34% |
| 38 | CG9268 | 62% | 33% |
| 39 | CG14217 | 60% | 14% |
| 40 | r-l | 59% | 11% |
| 41 | l(2)tid | 58% | 31% |
| 42 | DNAseII | 56% | 38% |
| 43 | NaCP60E | 56% | 10% |
| 44 | mnd | 54% | −6% |
| 45 | kis | 45% | 15% |

Example 3

Genetic Method of Identifying Nucleic Acid Sequences Associated with Sleep

Figure 3:
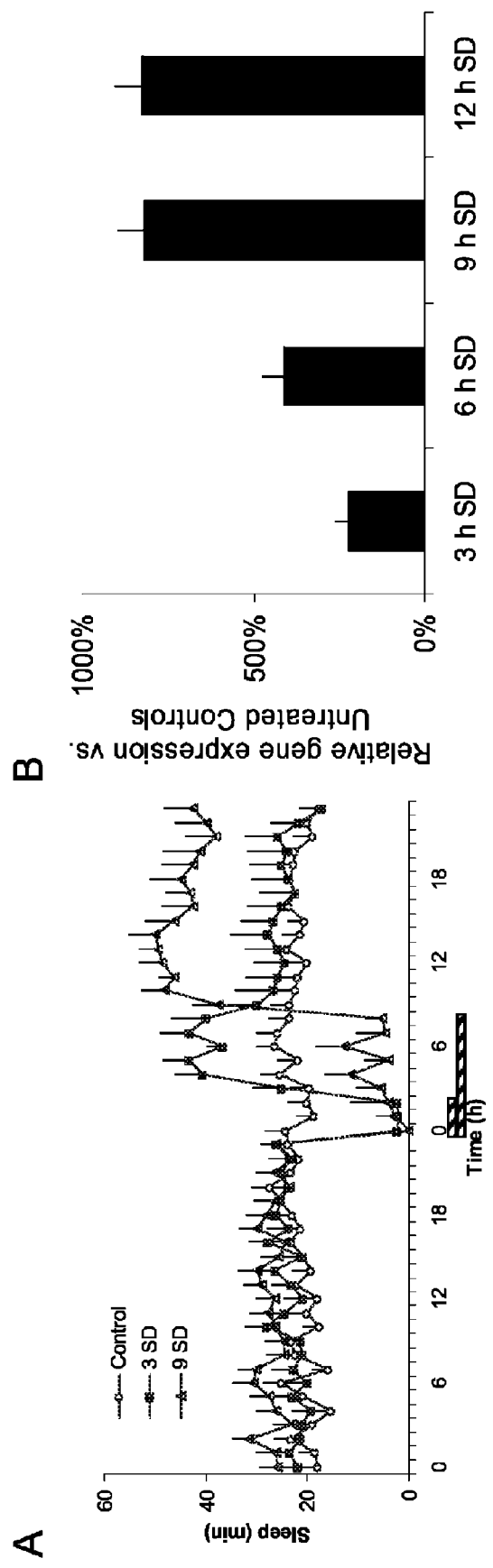
FIG. 3 depicts the temporal dynamics of gene expression in $cyc^{01}$ mutants. Minutes of sleep each hour for $cyc^{01}$ flies that have been deprived of sleep for 3 h (squares) and 9 h (triangles) and their untreated controls (circles) (FIG. 3A). Note that sleep does not return to baseline following 9 h of waking. Hatched bars indicate timing of the deprivation; 6 and 12 h data not shown to avoid clutter. Relative expression of CG18640 vs. untreated controls in $cyc^{01}$ flies immediately following 3, 6, 9 and 12 h of sleep deprivation as assessed using qPCR (FIG. 3B). CG18640 encodes a protein that binds calcium ions and displays α-amylase activity.

The search for genes associated with increased sleep drive began in cyc$^{01}$ flies that had been awake for 7 h. Previous results indicated that when the length of the deprivation was extended to 6 h and beyond, cyc$^{01}$ flies exhibited a large sleep rebound, but unlike shorter deprivations, the amount of sleep during recovery remained high and never returned to pretreatment levels (FIG. 3A; Shaw, P J et al., 2002. Nature 417: 287-291). The data further suggested that the detrimental effects of waking are accelerated in cyc$^{01}$ flies, and in addition, that these processes subsequently increase the need for sleep. To determine if a gene is indeed responsive to increasing levels of sleep debt, it is important to evaluate its temporal dynamics in response to increasing amounts of waking. Thus using the protocol described above, RNA was extracted from whole heads of flies that had been sleep deprived for 3, 6, 9 and 12 h and evaluated the expression patterns of select genes using qPCR. As before, one third of the sleep deprived cyc$^{01}$ flies and their untreated controls remained in the monitors so that we could evaluate their homeostatic response. FIG. 3B shows the expression profile of CG18640, an amylase, which is closely associated with the deleterious effects of prolonged waking.

Figure 4:
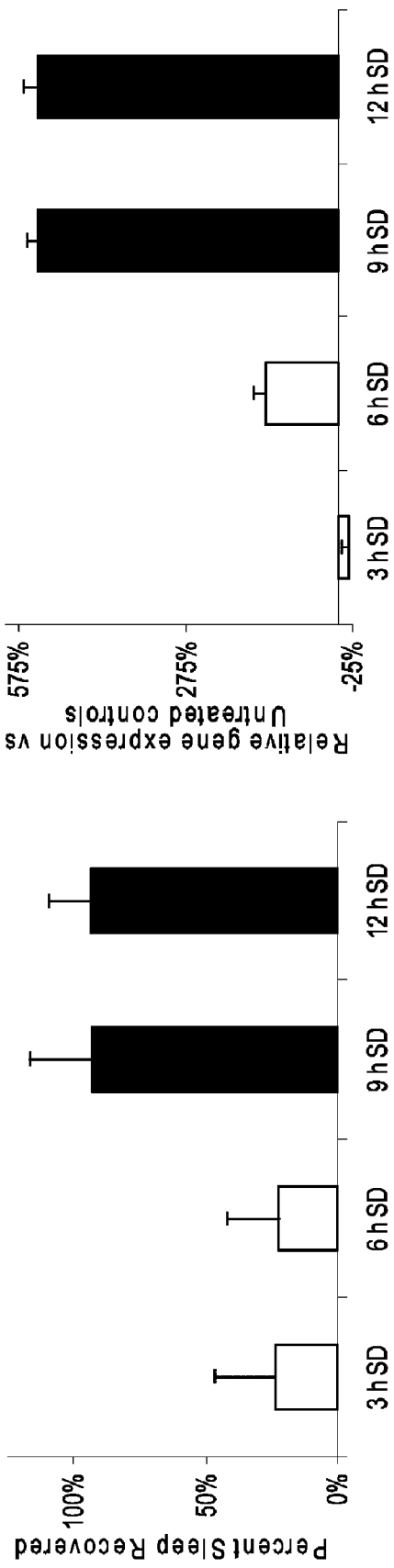
FIG. 4 illustrates that genes associated with homeostatic drive are not modified by 3 and 6 h of sleep deprivation in $tim^{01}$ mutants. $tim^{01}$ flies do not show a homeostatic response following 3 and 6 h of SD but show a normal rebound following 9 and 12 h of SD (FIG. 4A). Sleep recovered was calculated as a ratio of the amount of sleep recovered divided by that lost. Relative expression of CG18640 vs. untreated controls in $tim^{01}$ flies immediately following 3, 6, 9 and 12 h of sleep deprivation as assessed by qPCR (FIG. 4B). CG18640 encodes a protein that binds calcium ions and displays α-amylase activity.

It has been hypothesized that genes that signal sleep drive will be selectively activated only during waking conditions that are followed by a sleep rebound. Given that tim$^{01}$ flies are specifically resistant to short-term sleep deprivation but exhibit a normal response following 9 and 12 h of sleep deprivation, one would expect to find a step function in the expression pattern of genes associated with homeostasis (FIG. 4A). Thus tim$^{01}$ flies were subjected to 3, 6, 9 and 12 h of sleep deprivation using the protocol outlined above and the expression patterns of select genes using qPCR were evaluated. FIG. 4B shows the expression profile of CG18640, an amylase, which is closely associated with periods of waking that are followed by a homeostatic response.

Figure 5:
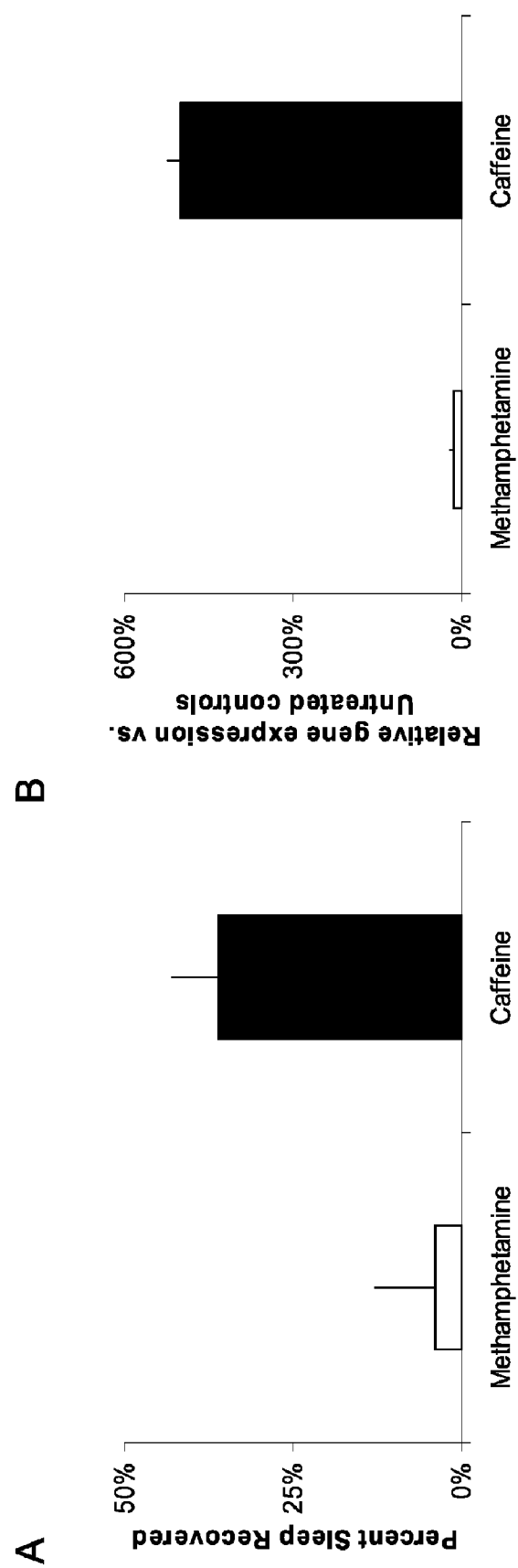
FIG. 5 illustrates that genes associated with homeostatic drive are not activated after 14 h of waking induced by methamphetamine. Percent of sleep recovered in wild-type flies following 14 h of wakefulness induced by caffeine (2 mg/mL) or methamphetamine (0.5 mg/mL) (FIG. 5A). Relative expression of CG18640 vs. untreated controls in wild-type flies immediately following 14 h of waking induced by caffeine or methamphetamine (FIG. 5B). CG18640 encodes a protein that binds calcium ions and displays α-amylase activity.

One might be concerned that 3-6 h of waking may not be sufficient to activate genes that are, in fact, only associated with waking and do not influence homeostasis. Sustained periods of waking in the fly can be induce pharmacologically (Hendricks, J C et al., 2000. Neuron 25: 129-138; Shaw, P J et al., 2000. Science 287: 1834-1837). Indeed, caffeine, methylphenidate, cocaine, amphetamine, methamphetamine (unpublished data) and modafinil (Hendricks, J C et al., 2003. Sleep 26: 139-146) all produce waking. Interestingly, while both caffeine and methamphetamine each produce sustained periods of waking and similar locomoter activity profiles, flies do not compensate for sleep lost during methamphetamine induced waking. Therefore wild-type flies were exposed to either caffeine or methamphetamine for 14 h and evaluated the magnitude of the homeostatic response. As above, gene expression was evaluated using qPCR and one third of the flies were allowed to recover for 24 h after drug removal and regular food was restored. Note that in contrast to clock mutants; wild-type flies only recover between 30-50% of their lost sleep when manually deprived, an observation that is true for caffeine (FIG. 5A) as well as methylphenidate, cocaine and amphetamine (Shaw, P J et. al., 2000. Science 287: 1834-1837). CG18640, an amylase, is an example of a gene whose expression pattern remains quite low even after 14 h of sustained waking as long as no homeostatic response has been recorded (FIG. 5B).

Example 4

Figure 6:
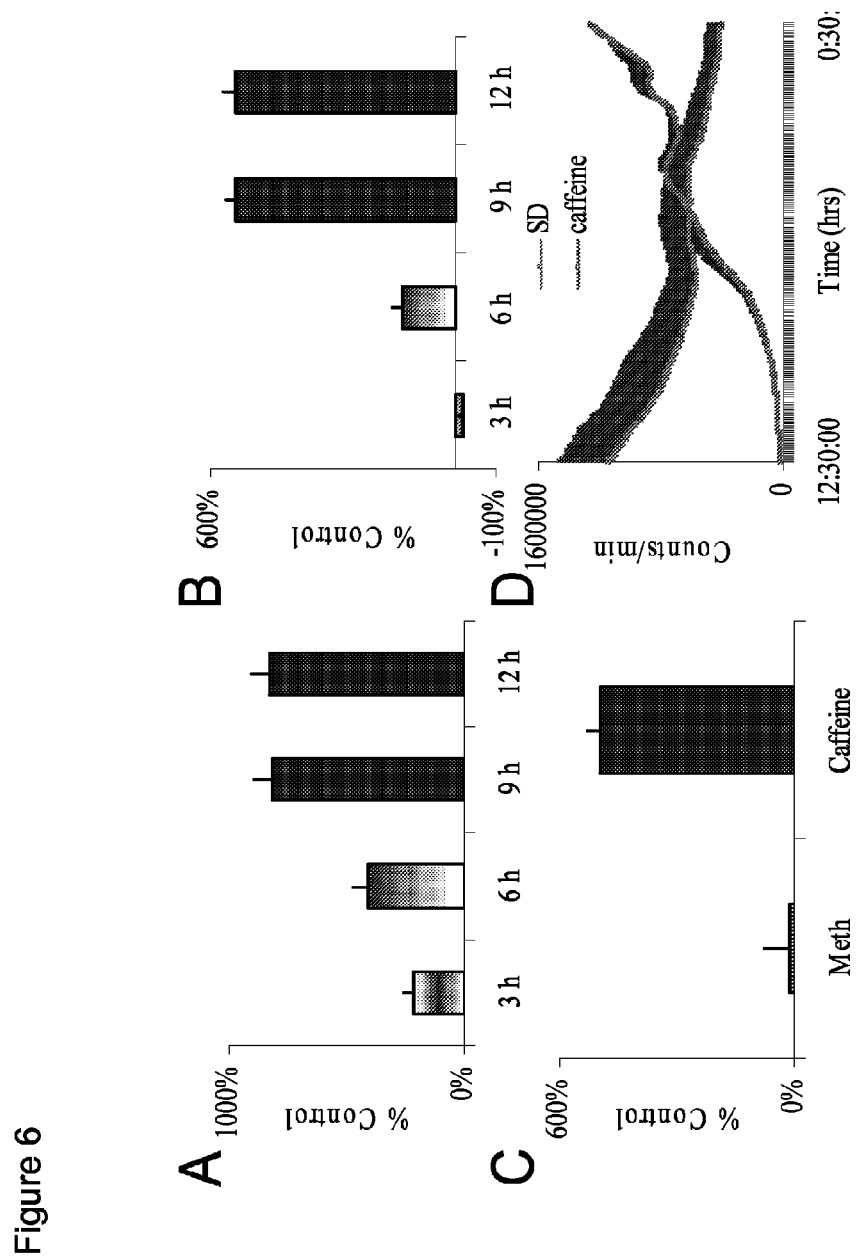
FIG. 6 illustrates that amylase can be used as a marker for sleep drive in Drosophila. Relative expression of Amylase mRNA extracted from whole heads is progressively increased following 3, 6, 9 and 12 hr of sleep deprivation in the sleep-loss sensitive mutant $cyc^{01}$ as assessed by qPCR (n=24/condition) (FIG. 6A). In the sleep-loss resistant mutant $tim^{01}$, mRNA levels for Amylase remain low following deprivations that do not activate homeostatic mechanisms (3 and 6 h SD; red bars), but are elevated following deprivations that activate homeostatic mechanisms (9 and 12 h SD; green bars) (FIG. 6B). Pharmacologically induced waking episodes that are not compensated by a homeostatic response (1 mg/ml methamphetamine; red bars) do not induce Amylase mRNA whereas pharmacologically induced waking episodes that are compensated by increased sleep (2.5 mg/mL caffeine, green bars) exhibit significant increases in Amylase mRNA (FIG. 6C). Bioluminescence (counts/min)) in Amy/Luc flies is high immediately following 12 h of sleep deprivation (n=9) and declines during recovery (blue) (FIG. 6D). In contrast, Amy/Luc flies that have slept all night and are placed onto caffeine (2.5 mg/ml) in the morning (n=9) show a progressive increase in bioluminescence as sleep debt accrues (green). Flies were maintained on 0.5% sucrose supplemented with 1 mM beetle luciferin.
Figure 9:
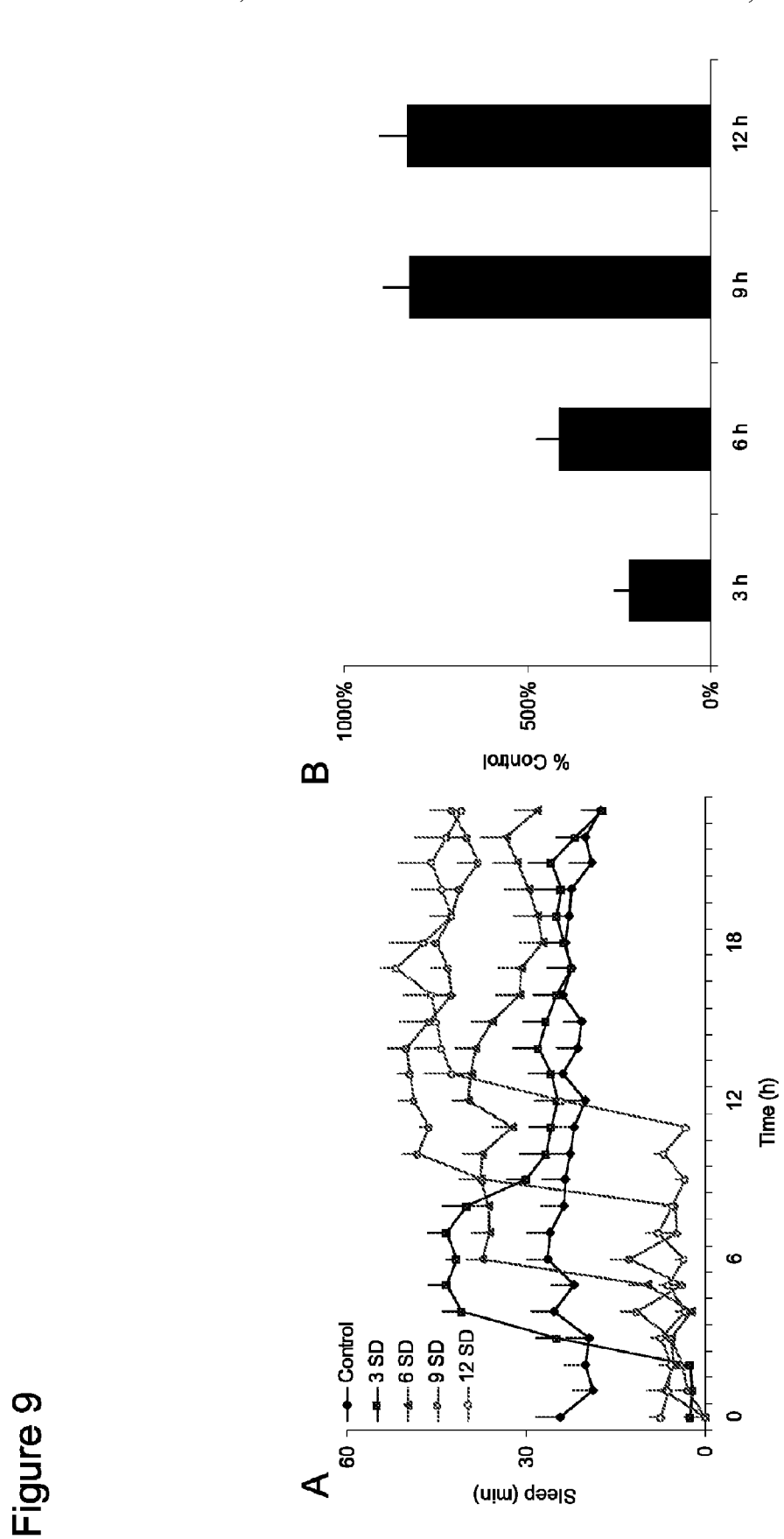
FIG. 9 depicts graphs demonstrating that Amylase is responsive to increasing levels of sleep debt. A) With increasing amounts of sleep loss, $cyc^{01}$ flies become longer sleepers. B) Relative expression of Amylase mRNA extracted from whole heads is progressively increased following 3, 6, 9 and 12 hr of sleep deprivation in the sleep-loss sensitive mutant $cyc^{01}$ as assessed by qPCR (n=24/condition).

Pharmacological Method of Identifying Nucleic Acid Sequences Associated with Sleep The reliability of Amylase as a biomarker of sleep drive was evaluated using genetic and pharmacological tools that differentially activate homeostatic mechanisms in the model organism *Drosophila melanogaster*. First the temporal dynamics of Amylase mRNA was evaluated in flies mutant for the canonical clock gene cycle (cyc$^{01}$) following 3, 6, 9 and 12 h of sleep deprivation (SD). The detrimental effects of waking are accelerated in cyc$^{01}$ mutants and accrue over the course of a short and well defined interval of 12 h (Hendricks, J C., et al., 2003. J Biol Rhythms 18: 12-25; Shaw, P J et. al., 2002. Nature 417: 287-291). As seen in FIG. 9A, even small amounts of sleep loss (3 h) result in large compensatory increases in sleep. Importantly, as $cyc^{01}$ flies experience greater amounts of sleep loss they become increasingly longer sleepers. As seen in FIG. 6A, Amylase mRNA levels increase progressively with the duration of waking indicating that it is responsive to increasing levels of sleep debt.

Figure 10:
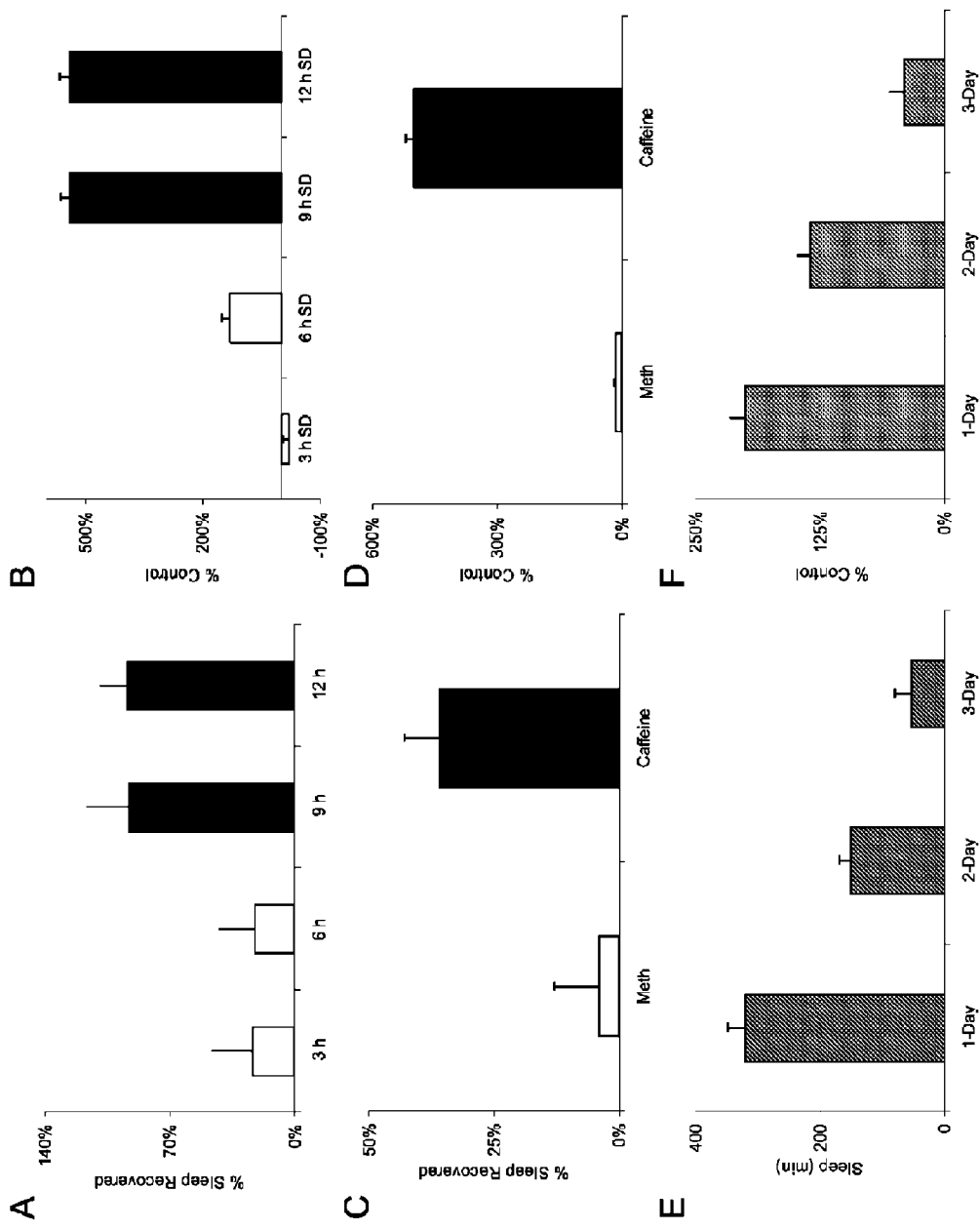
FIG. 10 depicts graphs demonstrating that Amylase is upregulated during waking conditions associated with sleepiness A) $tim^{01}$ flies show a minimal sleep rebound following 3 and 6 h of sleep deprivation (white bars) but generate a sleep rebound typical of other clock mutants following 9 and 12 h of SD (black bars). Percentage of sleep recovered is calculated as a ratio of the amount of sleep recovered divided by that lost. B) Amylase mRNA levels remain low following deprivations that do not activate homeostatic mechanisms (3 and 6 h SD; white bars), but are elevated following deprivations that activate homeostatic mechanisms (9 and 12 h SD; black bars). C) Waking induced by methamphetamine (1 mg/ml methamphetamine; white bars) do not induce a homeostatic response while waking induced by caffeine (2.5 mg/ml caffeine, black bars) exhibit a rebound of similar magnitude as that seen following manual SD. D) Amylase is elevated following caffeine administration but not after waking induced by methamphetamine. E) Daytime sleep is highest in young flies and declines to stable adult values by 3-days of age. F) Amylase levels decline with sleep time. Data are presented as percentage of 5 day old flies.

Next, whether amylase expression is associated with sleep homeostasis or whether it is non-specifically activated by waking was evaluated. The temporal dynamics of Amylase expression in flies mutant for timeless ($tim^{01}$) following 3, 6, 9 and 12 h of SD was evaluated. $tim^{01}$ flies are specifically resistant to short-term SD (3 and 6 h) but exhibit a normal homeostatic response following 9 and 12 hours of SD (Hendricks, J. C, et al., 2000. Neuron 25: 129-138; Shaw, P J et al., 2002. Nature 417: 287-291). As seen in FIG. 6B, Amylase mRNA levels are elevated following SD durations that activate sleep homeostatic mechanisms (9 and 12 h SD, black bars). To determine whether these results can be generalized to other experimental conditions, periods of waking that differentially activate sleep homeostasis were induced using the pharmaceuticals caffeine and methamphetamine. Both caffeine and methamphetamine each produce sustained periods of waking and similar locomotor activity profiles. However, unlike caffeine, flies do not compensate for the lost sleep accrued during methamphetamine induced waking (Andretic R, et al., 2005. Curr Biol 15: 1165-1175; Hendricks, J. C, et al., 2000. Neuron 25: 129-138; SHAW, P J, et al., 2000. Science 287: 1834-1837). As seen in FIGS. 6C and 10D, Amylase expression is strongly activated by caffeine but not by methamphetamine. To determine whether Amylase levels are associated with naturally occurring conditions where sleep drive is high, we evaluated its progression during the first few days of the flies' adult life. Flies, like humans, exhibit ontogenetic variations in brain plasticity that are associated with increased sleep time (Shaw et al., 2000. Science 287: 1834-7; Balling et al., 1987. J Neurogenet 4:65-73). As seen in FIG. 10E daytime sleep was high immediately after eclosion and declined to adult levels by 3-days of age. Interestingly, the levels of Amylase followed these naturally occurring changes in sleep time (FIG. 10F). Together with results obtained in $tim^{01}$ mutants, the data indicate that Amylase is not simply a marker for waking but for conditions where sleep drive is elevated.

Figure 11:
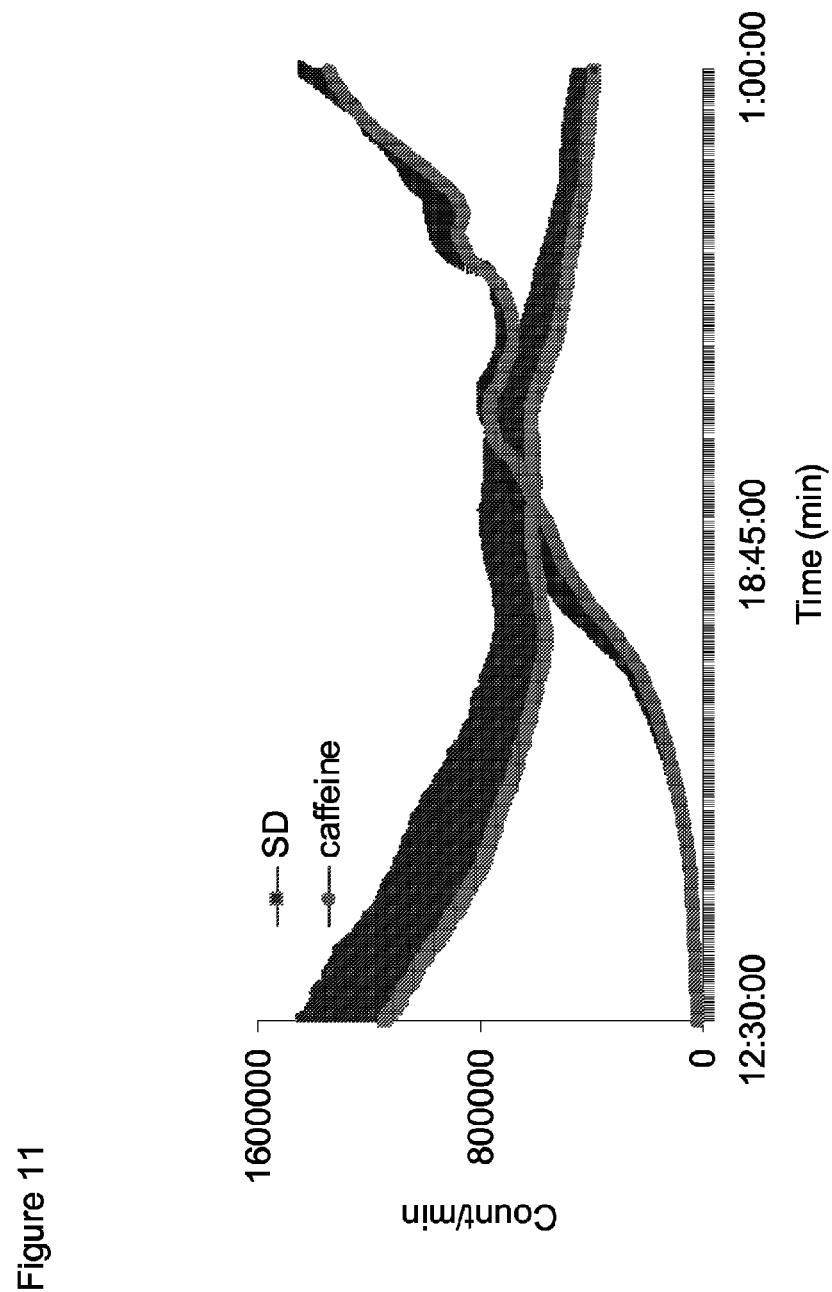
FIG. 11 depicts a graph showing that Amylase can provide an assessment of sleep drive in real-time A.) Bioluminescence (counts/min±SEM) in Amy/Luc flies is high immediately following 12 h of sleep deprivation (n=9) and declines during recovery (blue). In contrast, Amy/Luc flies that have slept all night and are placed onto caffeine (2.5 mg/ml) in the morning (n=9) show a progressive increase in bioluminescence as sleep debt accrues (green). Flies were maintained on 0.5% sucrose supplemented with 1 mM beetle luciferin.

To determine whether amylase can provide an assessment of sleep drive in real-time, a Drosophila line in which the promoter for amylase was linked to the firefly luciferase (Amy/Luc) was evaluated (Hickey, D A, et al., 1994. Proc Natl Acad Sci USA 91: 11109-11112). Bioluminescence was monitored for 12 h throughout recovery following 16 h of SD and in siblings placed onto caffeine following a full night's sleep. As seen in FIGS. 6D and 11, bioluminescence is high immediately following 16 h of SD and declines during recovery (blue line). In contrast, bioluminescence was low following a full nights sleep and increased as the animals spent more time on caffeine consistent with the effects of caffeine described above (green line). Thus, changes in bioluminescences are correlated with rising and falling levels of sleep drive in real-time.

Example 5

Figure 7:
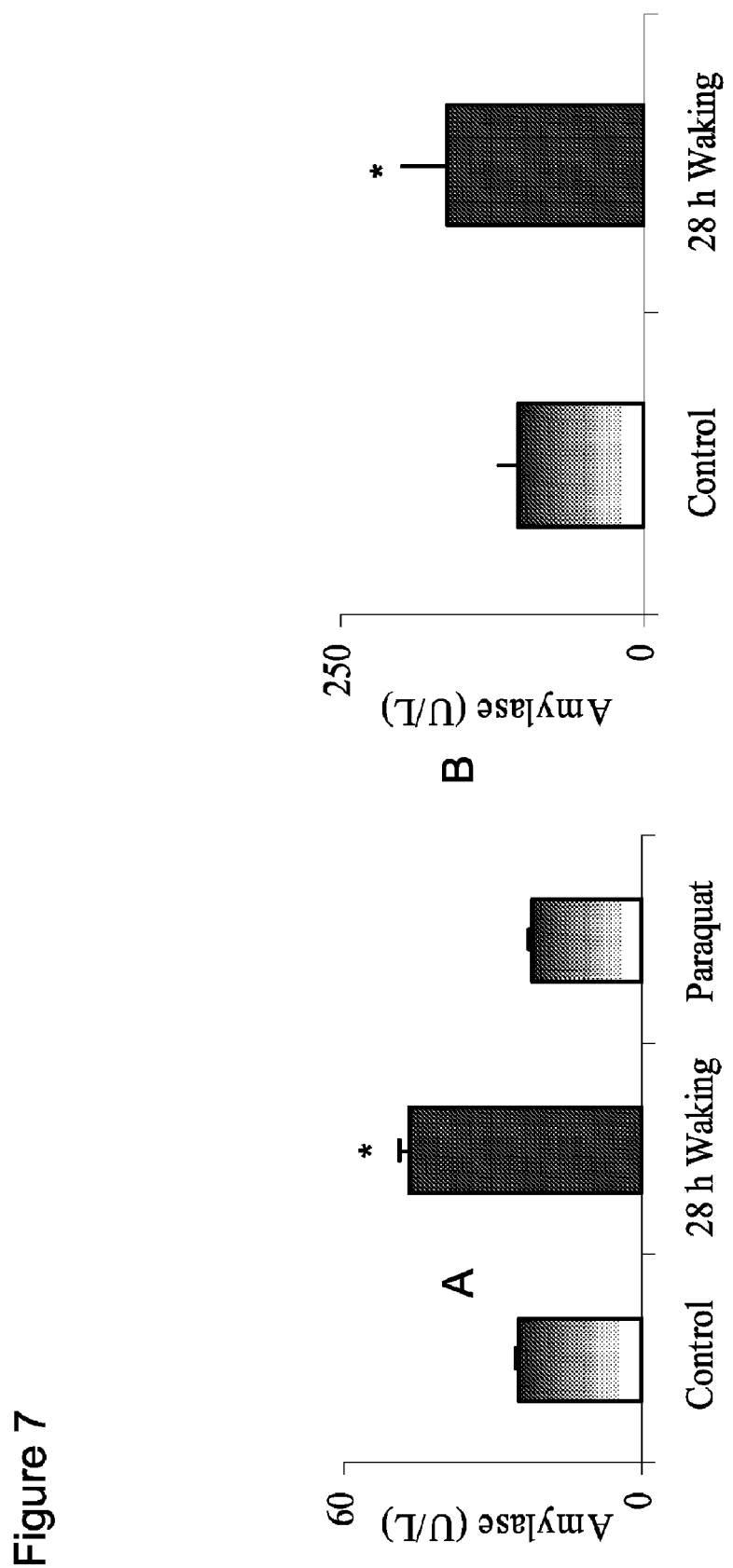
FIG. 7 illustrates that amylase can be used as a marker for sleep drive in Humans. Amylase activity, but not protein levels are increased in homogenates from Drosophila heads following 28 h of enforced waking (n=20) and in saliva samples taken from normal healthy humans (n=9) following 28 h of waking ($*p<0.05$); 20 μM paraquat did not alter amylase activity (FIG. 7A). Human saliva samples were collected at the same circadian time over consecutive weekends where each subject served as their own untreated control (FIG. 7B).
Figure 8:
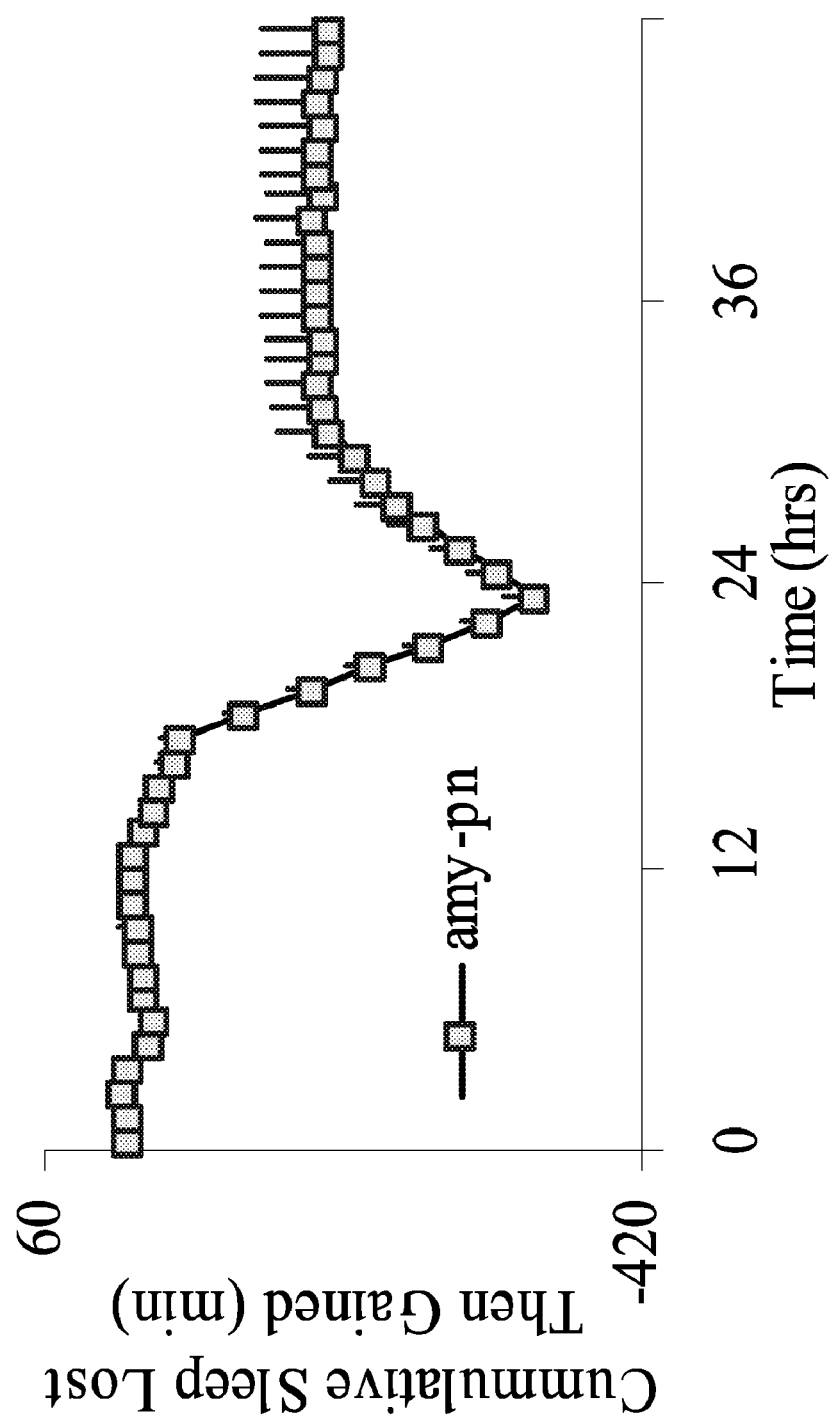
FIG. 8 depicts cumulative sleep loss or gain in the amy-$p^n$ mutant. Cumulative sleep lost then gained following 6 h of sleep deprivation in the amy-p mutant. A negative slope indicates sleep lost, a positive slope indicates sleep gained; when the slope is zero recovery is complete. These data suggest that amylase is not mechanistically involved in sleep regulation even though its mRNA and activity levels are tightly correlated with sleep drive.
Figure 12:
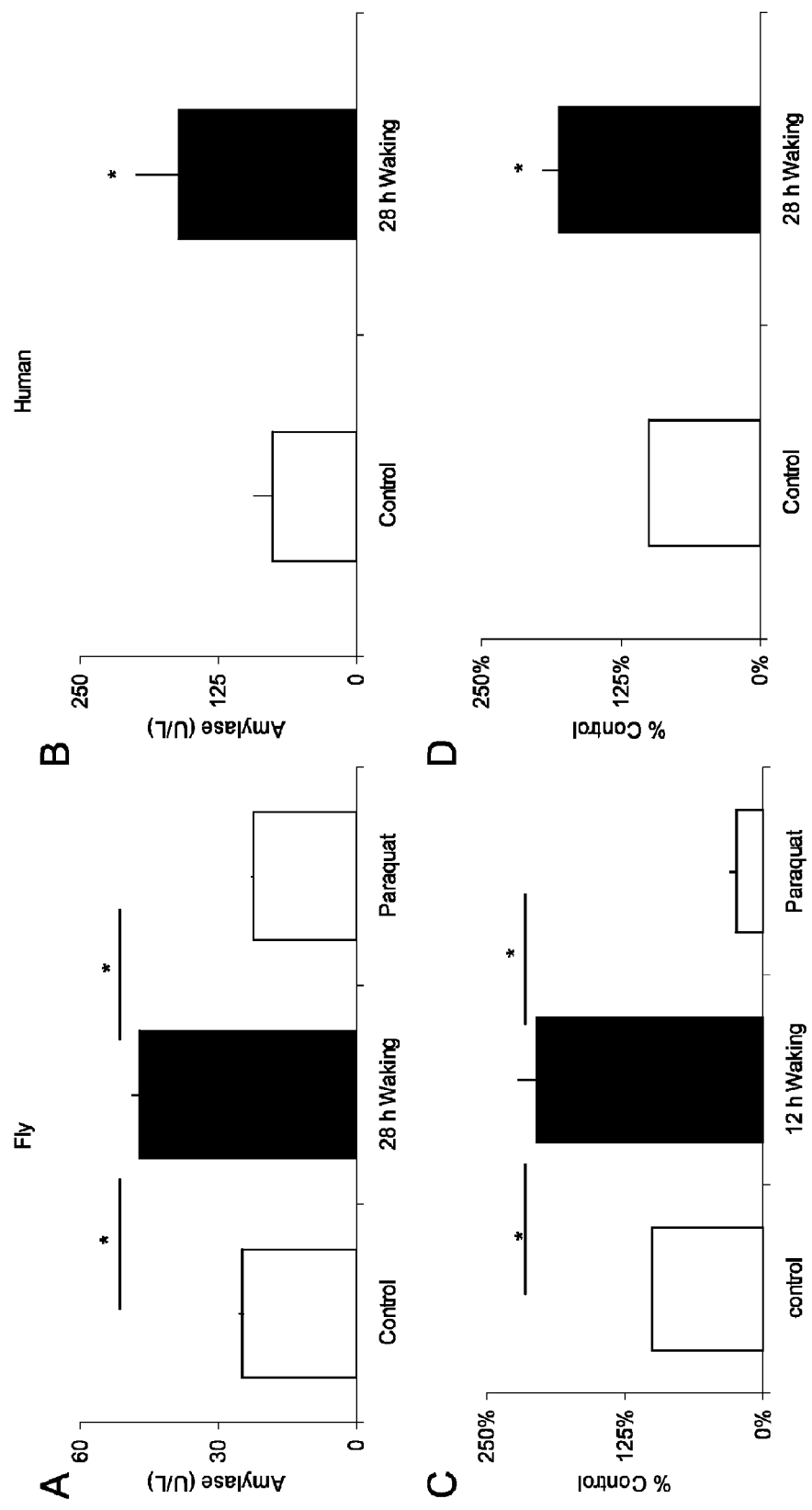
FIG. 12 depicts graphs demonstrating that Amylase can be used as a marker in flies and humans A, B) Amylase activity, but not protein levels are increased in homogenates from Drosophila heads following 28 h or enforced waking (n=20) and in saliva samples taken from normal healthy humans (n=9) ($*p<0.05$). In flies, 20 μM paraquat did not alter Amylase activity. Human saliva samples were collected at the same circadian time over consecutive weekends where each subject served as their own untreated control. C, D) Amylase mRNA, is increased in homogenates from Drosophila heads following 28 h or enforced waking (n=20) and in saliva samples taken from normal healthy humans (n=6) following 28 h of waking ($*p<0.05$).
Figure 13:
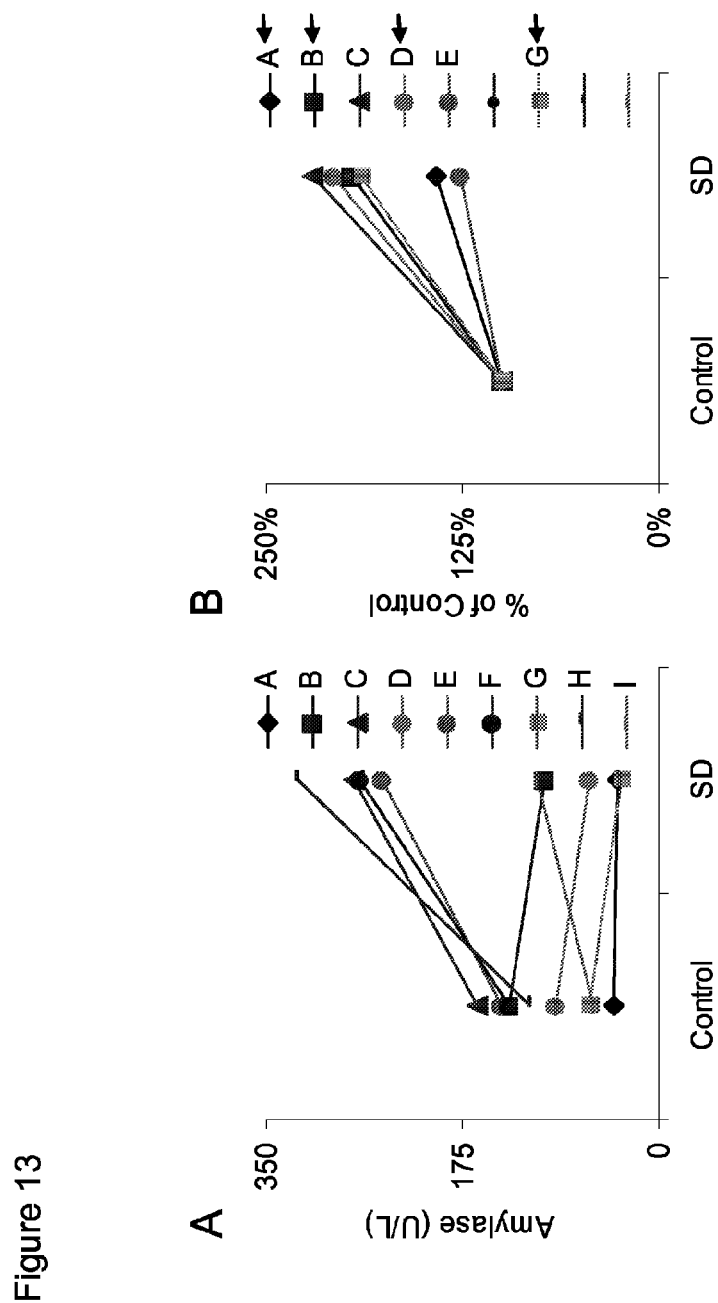
FIG. 13 depicts graphs of individual differences in Amylase levels. A) Amylase activity was increased in 5 of 9 subjects after 28-h of waking B) Amylase mRNA levels were increased in all 6 saliva samples with intact β-actin. Arrows designate subjects with Amylase activity levels that were not elevated but that displayed increases in Amylase mRNA.

As seen in FIGS. 7A and B amylase activity is increased in both humans (FIG. 7A) and flies (FIG. 7B) following 28 h of sustained waking compared to untreated circadian-matched controls; total protein and saliva volume were not significantly altered (p>0.10, data not shown). Human saliva was evaluated for markers of sleep drive because brainstem nuclei regulating salivary gland activity receive inputs from neural structures in the forebrain that are centers for homeostatic regulation (Bosch, et. al., 2002. Int Rev Neurobiol 52: 213-253; Jansen, A S, et al., 1992. Brain Res 572: 253-260). In flies, paraquat did not alter amylase activity suggesting these changes were not due to stress. Moreover, in humans, shorter amounts of SD (<8 hr) do not activate salivary amylase activity consistent with a previous report (Parkkila, S, et al., 1995. Acta Physiol Scand 154: 205-211). Thus, it is unlikely that stress plays a role in modifying amylase activity during sustained periods of waking in either humans or flies. Therefore, we evaluated Amylase mRNA levels in our sleep deprived subjects. To ensure that the integrity of mRNA was consistent between subjects, only samples with intact β-actin were evaluated (Park et al., 2006. Clin Chem 52:988-94). As seen in FIG. 12, Amylase mRNA was increased approximately 2-fold in both humans and flies after sleep deprivation. Together these data indicated that, as a group, Amylase activity and mRNA levels are elevated by sustained waking in humans. Since, individuals vary greatly in their response to sleep loss (Van Dongen et al., 2005. Sleep 28:479-96) it is important to present data from individual subjects. As seen in FIG. 13A, Amylase activity is elevated in 5 of 9 subjects. In contrast, all subjects with intact salivary mRNA showed increased Amylase mRNA levels, including 4 subjects whose Amylase activity was not elevated (FIG. 13B). Interestingly, data from both the fly and human suggest that Amylase mRNA is a more sensitive measurement of sleepiness than Amylase activity.

What is claimed is:

1. A method for identifying a subject that is awake and sleep deprived, the method comprising:
    (a) collecting a biosample from the subject,
    (b) processing the biosample to measure the level of amylase,
    (c) measuring the level of amylase in the biosample,
    (d) comparing the level of amylase in the biosample to a baseline level of amylase, and
    (e) identifying the awake subject as sleepy and sleep deprived if the biosample has an elevated level of amylase compared to a baseline level of amylase.

2. The method of claim 1, wherein the biosample is selected from the group consisting a blood sample, an interstitial fluid sample, a saliva sample, a urine sample, and a pancreatic sample.

3. The method of claim 1, wherein the biosample is a saliva sample.

4. The method of claim 1, wherein the level of amylase measured is selected from the group consisting of the level of amylase mRNA, the level of amylase transcription, the level of amylase translation, the level of amylase protein, and the level of amylase activity.

5. The method of claim 1, wherein the level of amylase mRNA is measured.

6. The method of claim 1, wherein the subject has been diagnosed as having a sleep disorder.

7. The method of claim 1, wherein the subject is at risk for sleepiness.

8. The method of claim 7, wherein sleepiness is a condition selected from the group consisting of coma, dyssomnias, parasomnias, and sleep disorders.

9. The method of claim 5, wherein the level of mRNA is measured by a technique selected from the group consisting of northern blot, microarray, expression profiling, nuclease protection assay, RNase protection assay, S1 nuclease protection assay, RT-PCR, quantitative RT-PCR, in situ hybridization, or variants thereof.

10. A method for diagnosing a sleep disorder in a subject, the method comprising:
    (a) collecting a biosample from the subject,
    (b) processing the biosample to measure the level of amylase,
    (c) measuring the level of amylase in the biosample,
    (d) comparing the level of amylase in the biosample to a baseline level of amylase, and
    (e) diagnosing a sleep disorder if the biosample has an elevated level of amylase compared to a baseline level of amylase.

11. The method of claim 1, wherein the biosample is selected from the group consisting a blood sample, an interstitial fluid sample, a saliva sample, a urine sample, and a pancreatic sample.

12. The method of claim 1, wherein the biosample is a saliva sample.

13. The method of claim 1, wherein the level of amylase measured is selected from the group consisting of the level of amylase mRNA, the level of amylase transcription, the level of amylase translation, the level of amylase protein, and the level of amylase activity.

14. The method of claim 1, wherein the level of amylase mRNA is measured.

15. The method of claim 14, wherein the level of mRNA is measured by a technique selected from the group consisting of northern blot, microarray, expression profiling, nuclease protection assay, RNase protection assay, S1 nuclease protection assay, RT-PCR, quantitative RT-PCR, in situ hybridization, or variants thereof.

* * * * *

UNITED STATES PATENT AND TRADEMARK OFFICE
CERTIFICATE OF CORRECTION

| | | |
|---|---|---|
| PATENT NO. | : 7,915,005 B2 | Page 1 of 1 |
| APPLICATION NO. | : 11/558074 | |
| DATED | : March 29, 2011 | |
| INVENTOR(S) | : Paul Shaw et al. | |

It is certified that error appears in the above-identified patent and that said Letters Patent is hereby corrected as shown below:

Column 20, line 46, after the text "consisting" insert -- of --

Signed and Sealed this
Eighth Day of November, 2011

David J. Kappos
*Director of the United States Patent and Trademark Office*